United States Patent [19]

Lee et al.

[11] Patent Number: 4,626,503
[45] Date of Patent: Dec. 2, 1986

[54] ANTITUMOR AGENTS LL-D49194$\alpha_1$, LL-D49194$\beta_1$, LL-D49194$\beta_2$, LL-D49194$\beta_3$, LL-D49194$\gamma$, LL-D49194$\delta$, LL-D49194$\epsilon$, LL-D49194$\xi$, LL-D49194$\eta$, LL-D49194$\omega_1$, LL-D49194$\omega_2$, AND LL-D49194$\omega_3$

[75] Inventors: May D. Lee, Monsey; Amedeo A. Fantini, New City, both of N.Y.; David P. Labeda, Peoria, Ill.; William M. Maiese, Bridgewater; Raymond T. Testa, Cedar Grove, both of N.J.; Donald B. Borders, Suffern, N.Y.

[73] Assignee: American Cyanamid Company, Stamford, Conn.

[21] Appl. No.: 701,831

[22] Filed: Feb. 14, 1985

Related U.S. Application Data

[63] Continuation-in-part of Ser. No. 596,499, Apr. 4, 1984, abandoned.

[51] Int. Cl.$^4$ ............... C12P 19/60; C12N 1/20; C07G 11/00; A01N 25/26
[52] U.S. Cl. ................... 435/75; 435/253; 536/16.8; 514/33; 424/116; 424/117; 424/118; 424/119
[58] Field of Search ............ 435/75, 253; 424/116, 424/117, 118, 119; 536/16.8; 514/33

[56] References Cited

U.S. PATENT DOCUMENTS 4,259,319  3/1981  Umezawa et al. ............ 424/117
4,420,473  12/1983  Umezawa et al. ............ 424/118
4,518,589  5/1985  Konishi et al. ............... 536/16.8

Primary Examiner—Alvin E. Tanenholtz
Attorney, Agent, or Firm—Edward A. Conroy, Jr.

[57] ABSTRACT

Antitumor agents LL-D49194$\alpha_1$, LL-D49194$\beta_1$, LL-D49194$\beta_2$, LL-D49194$\beta_3$, LL-D49194$\gamma$, LL-D49194$\delta$, LL-D49194$\epsilon$, LL-D49194$\xi$, LL-D49194$\eta$, LL-D49194$\omega$, LL-D49194$\omega_2$ and LL-D49194$\omega_3$.

19 Claims, 34 Drawing Figures

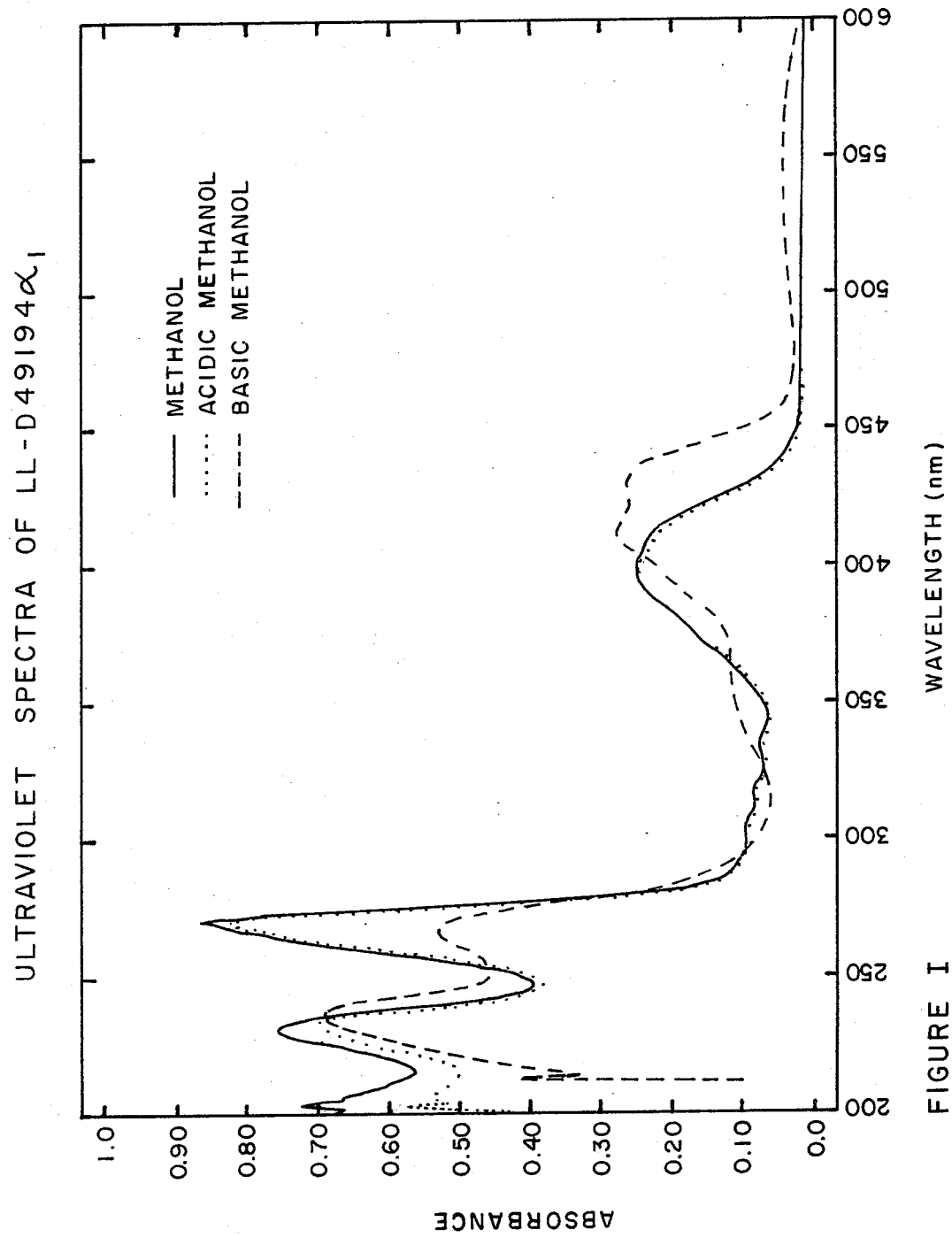

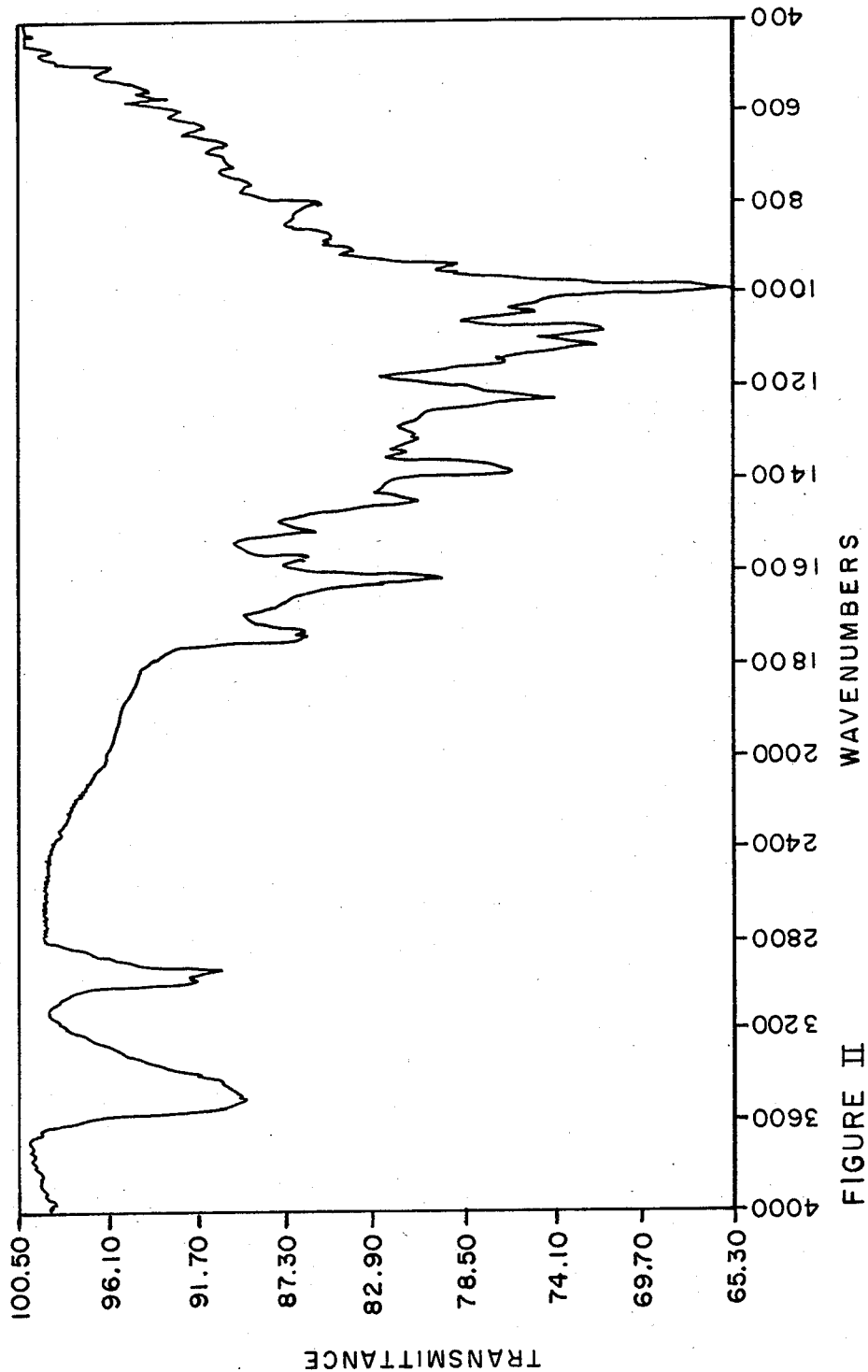

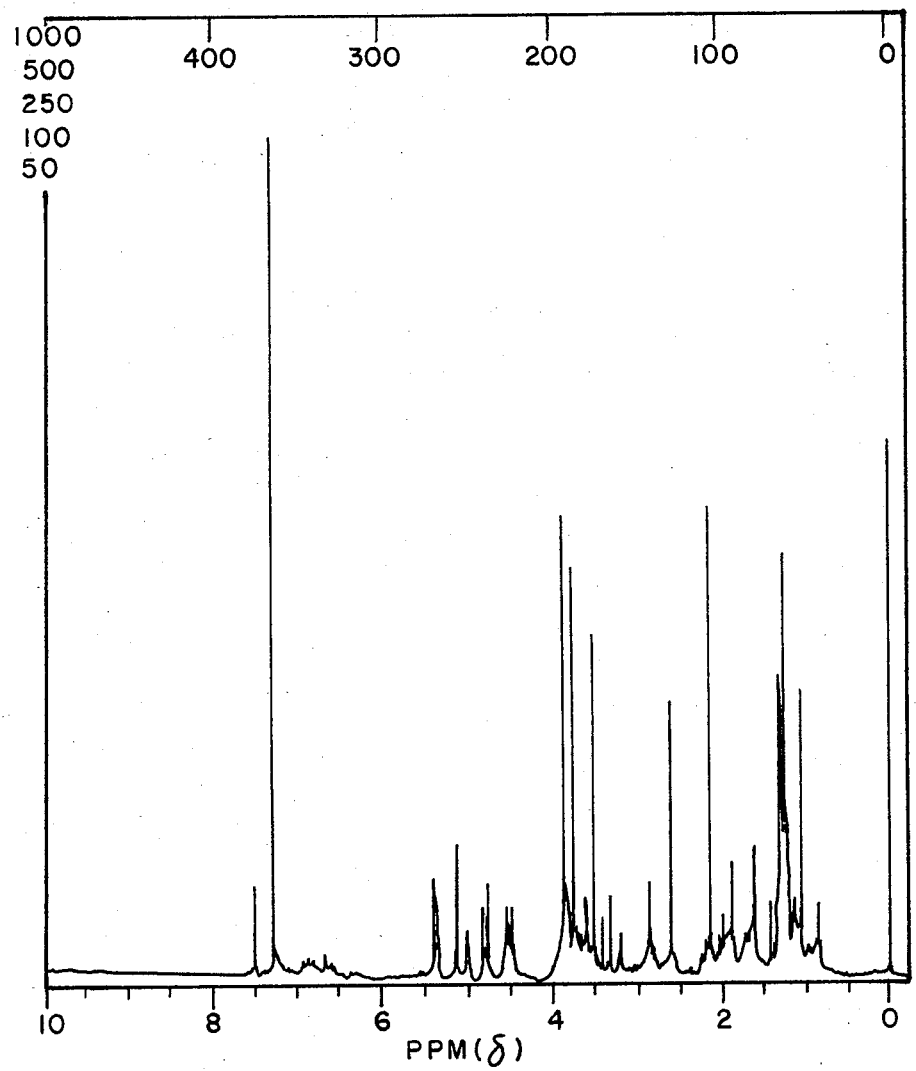
FIGURE III

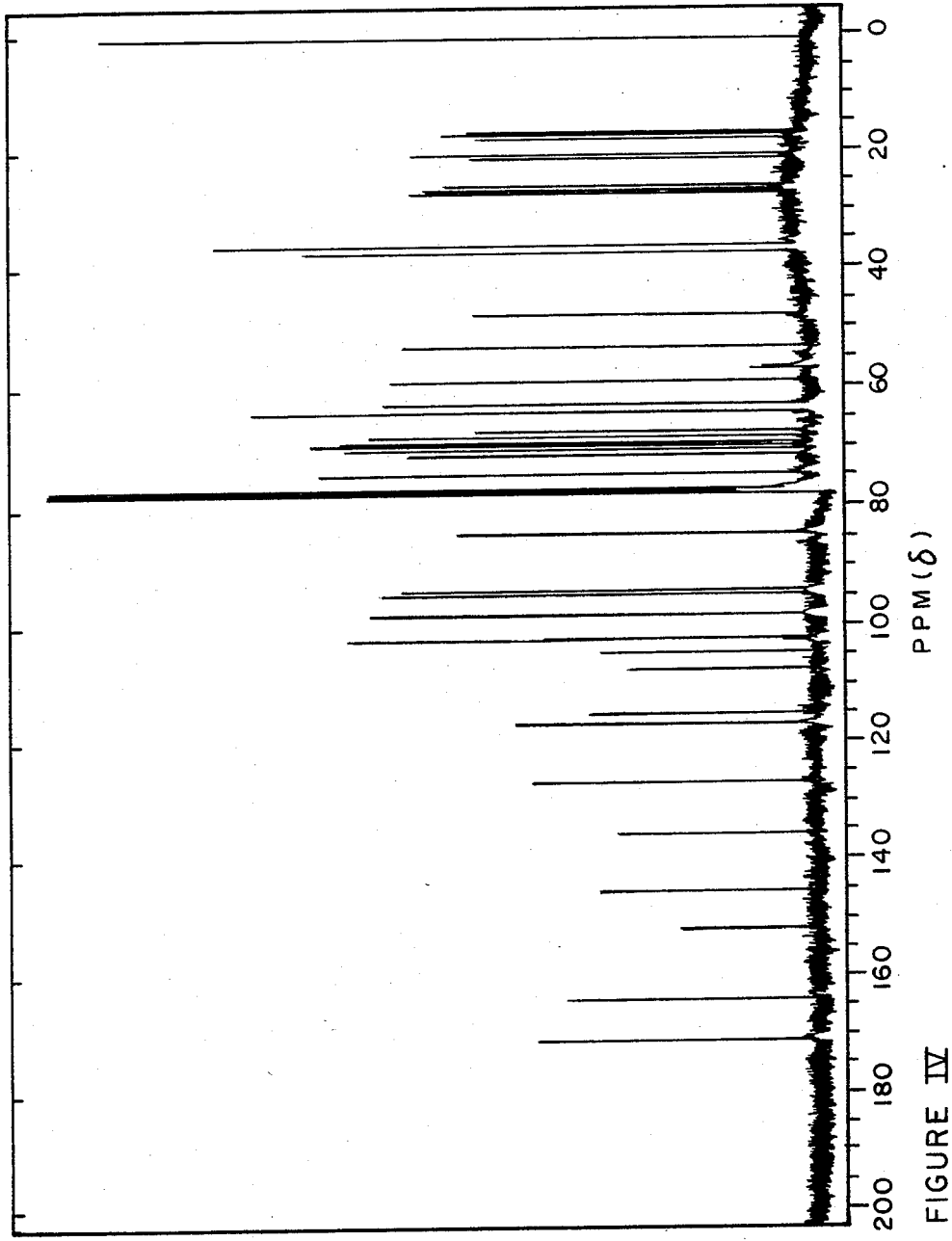
FIGURE IV

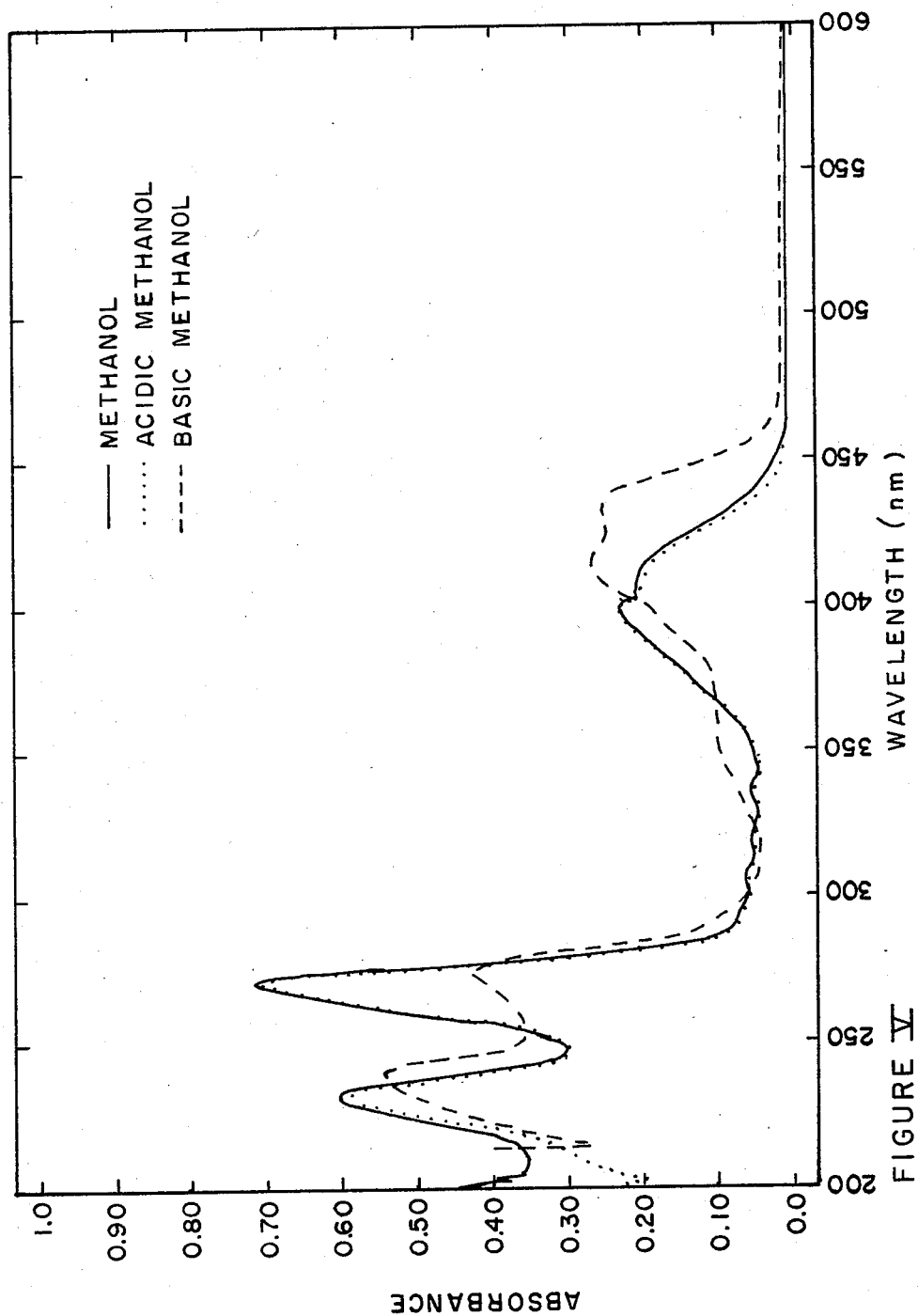

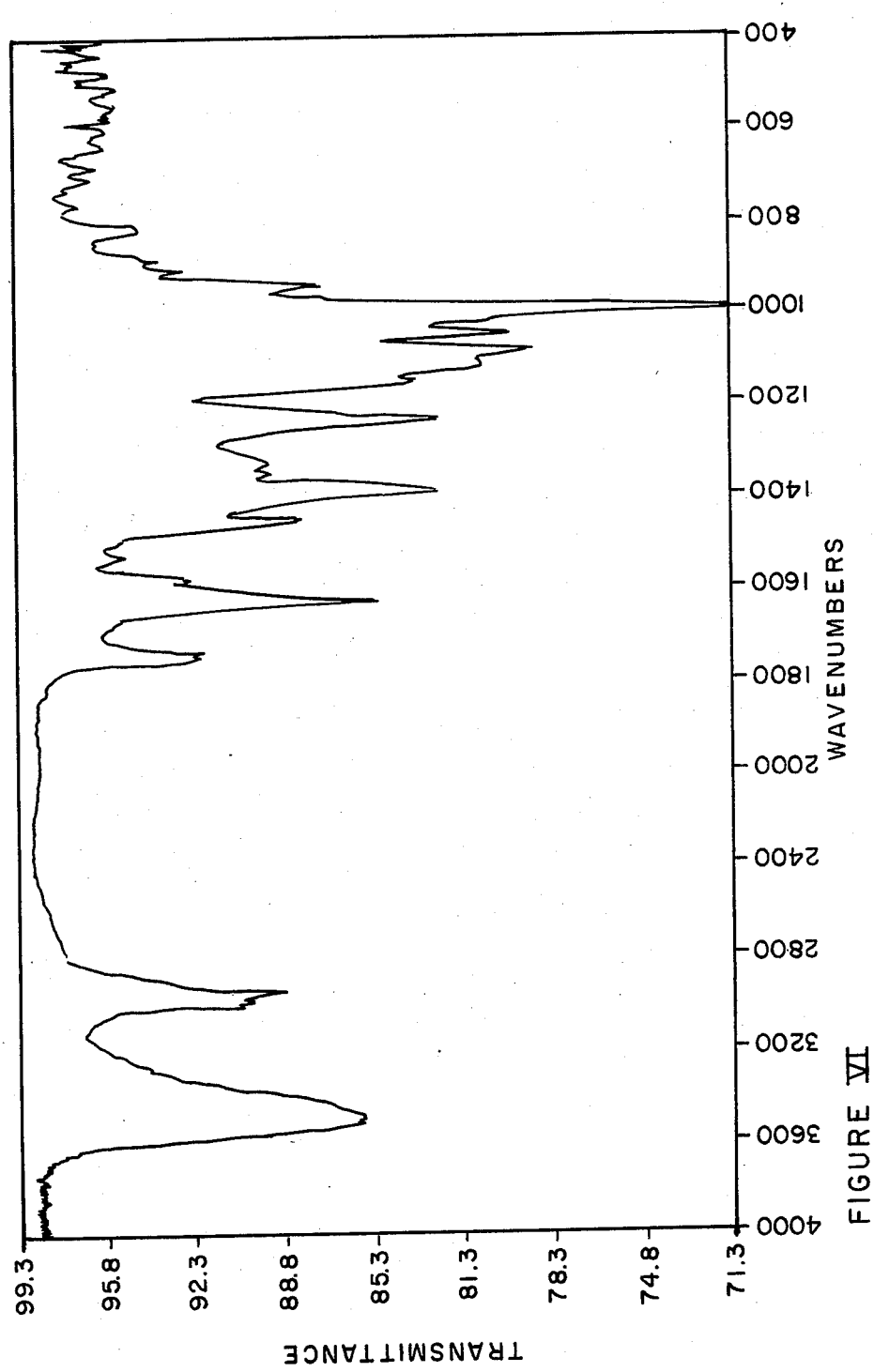

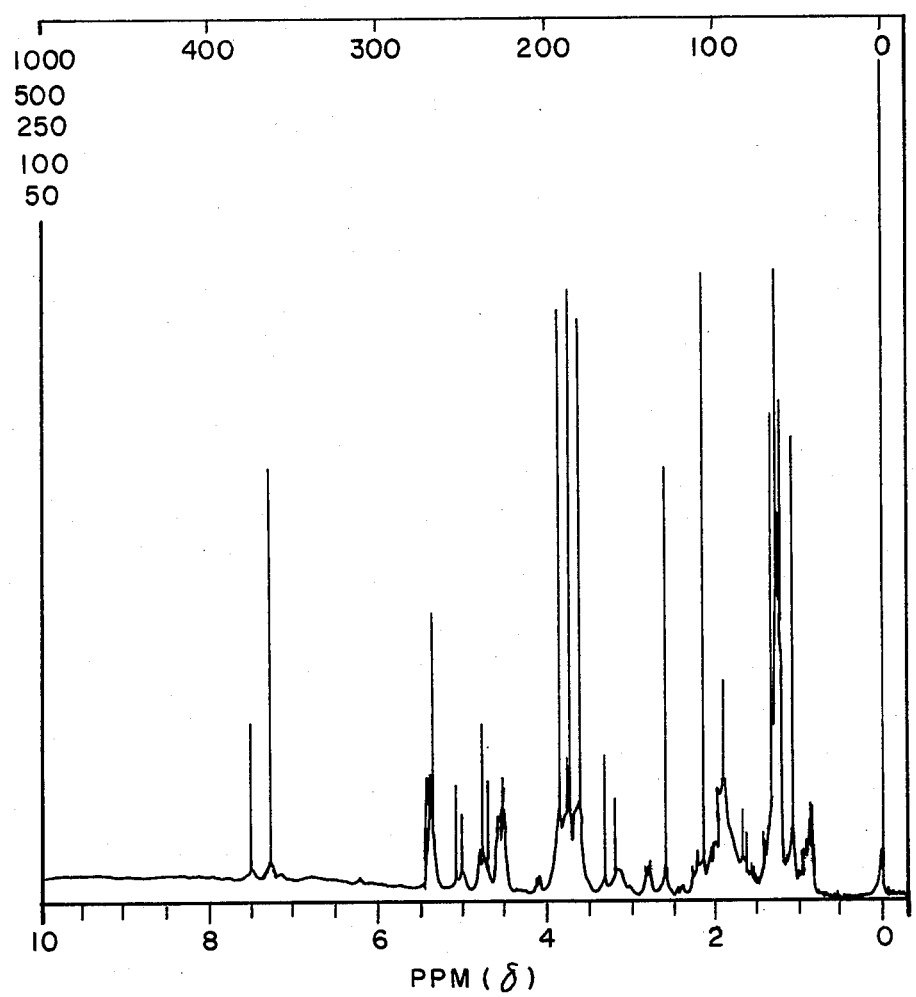

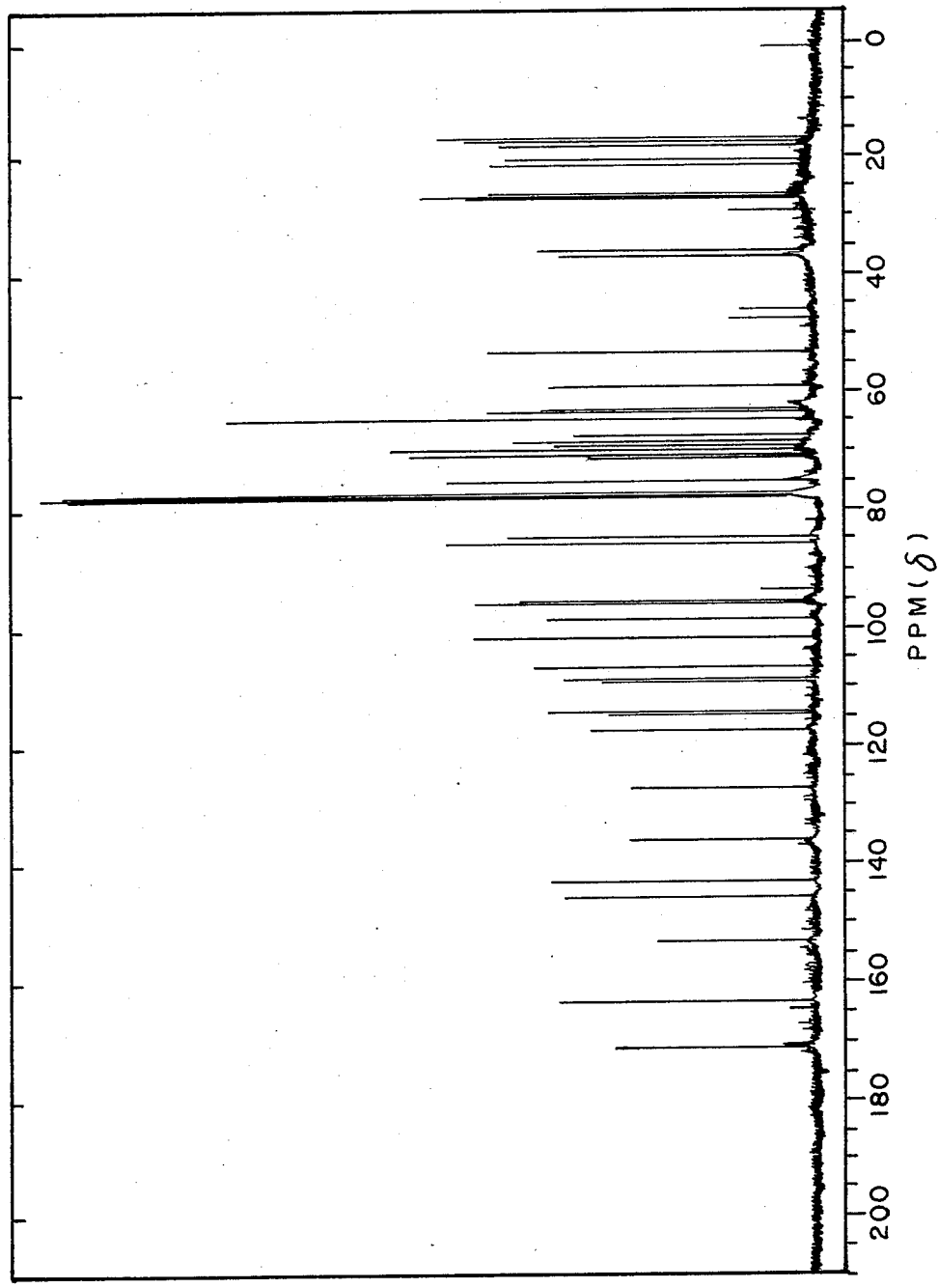

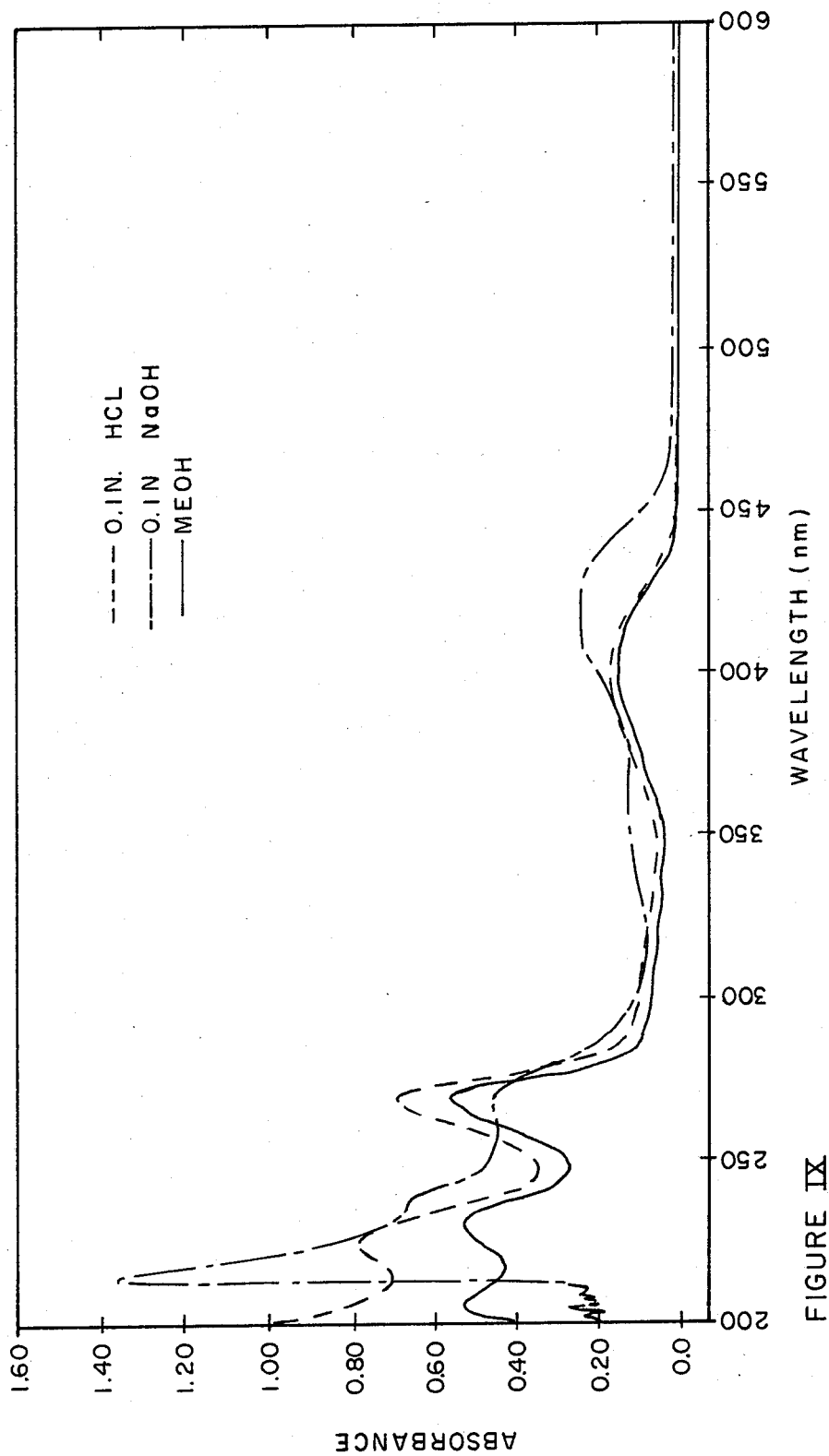
FIGURE IX

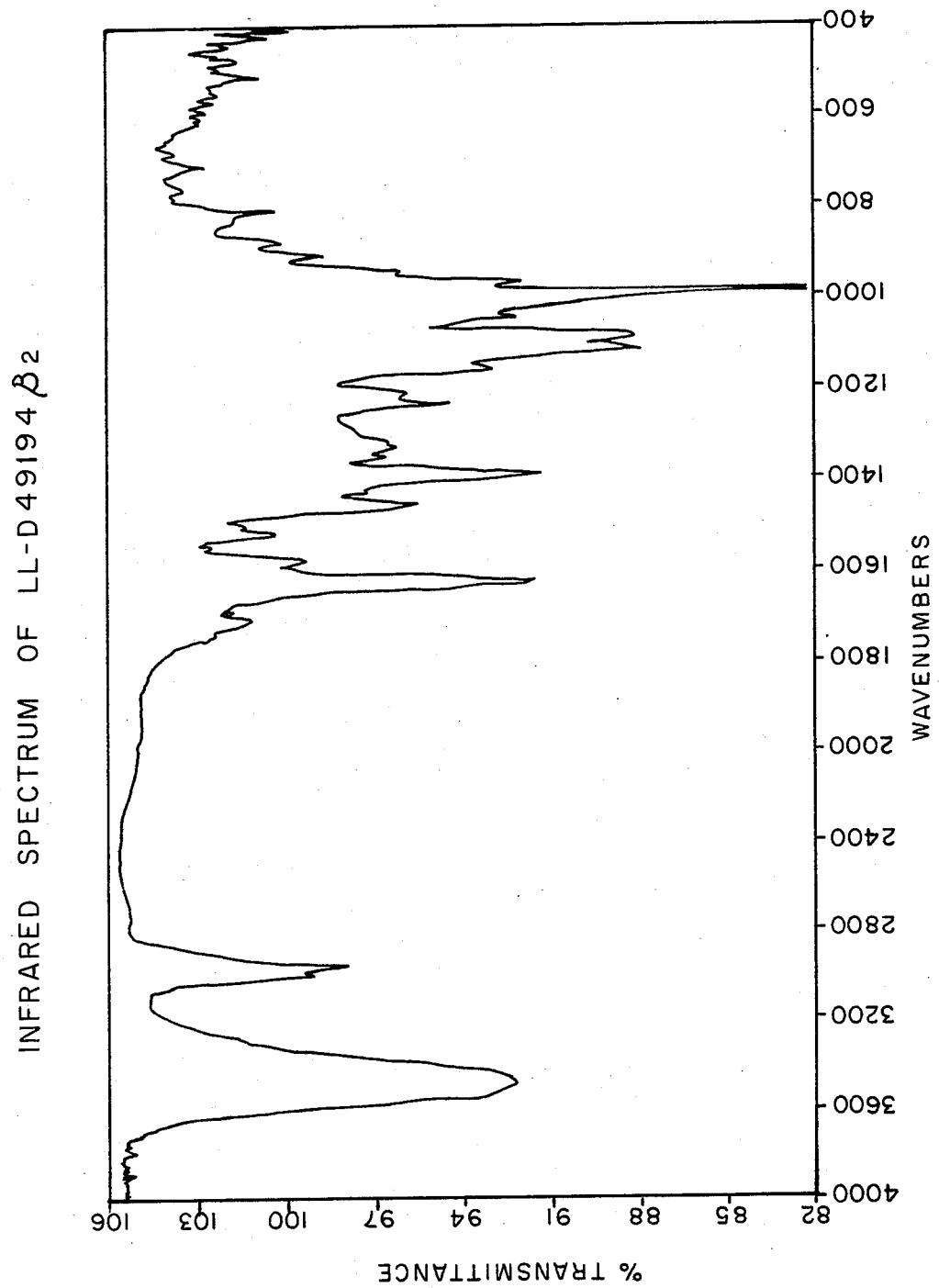
FIGURE X

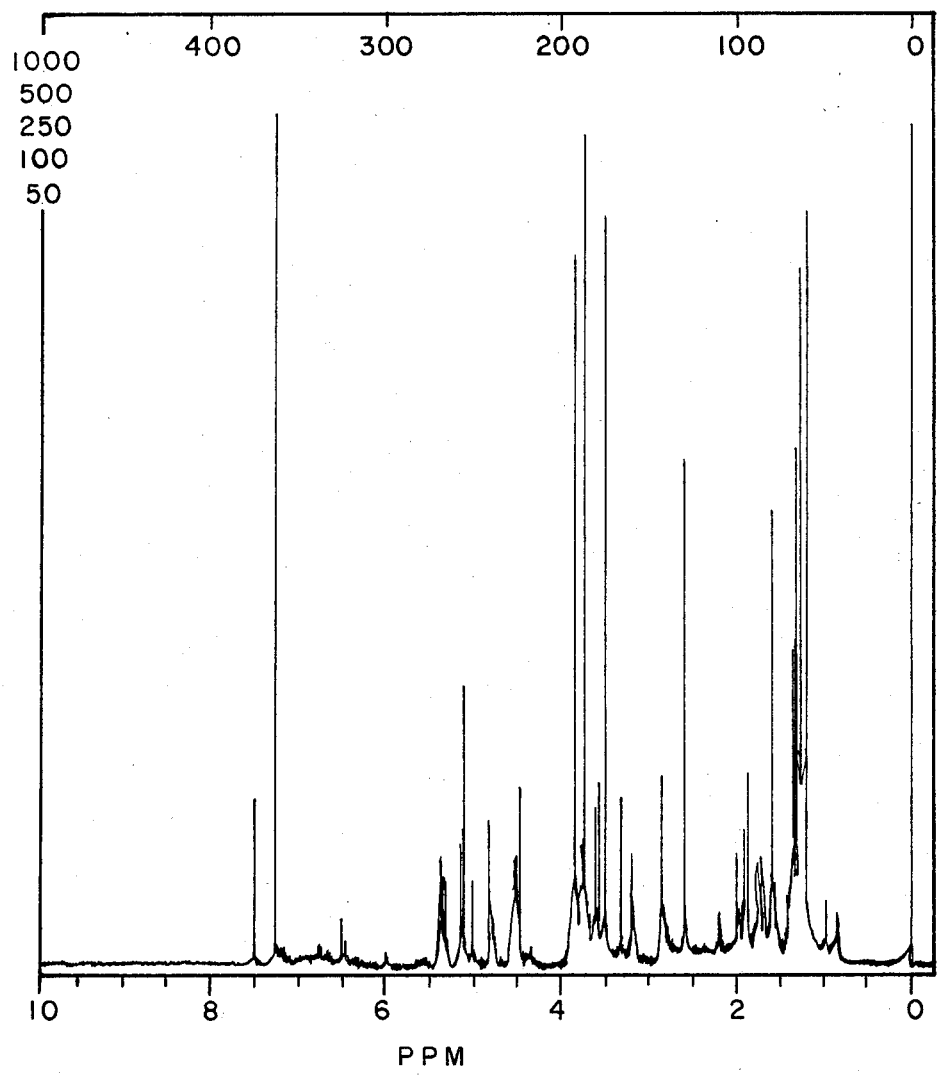
FIGURE XI

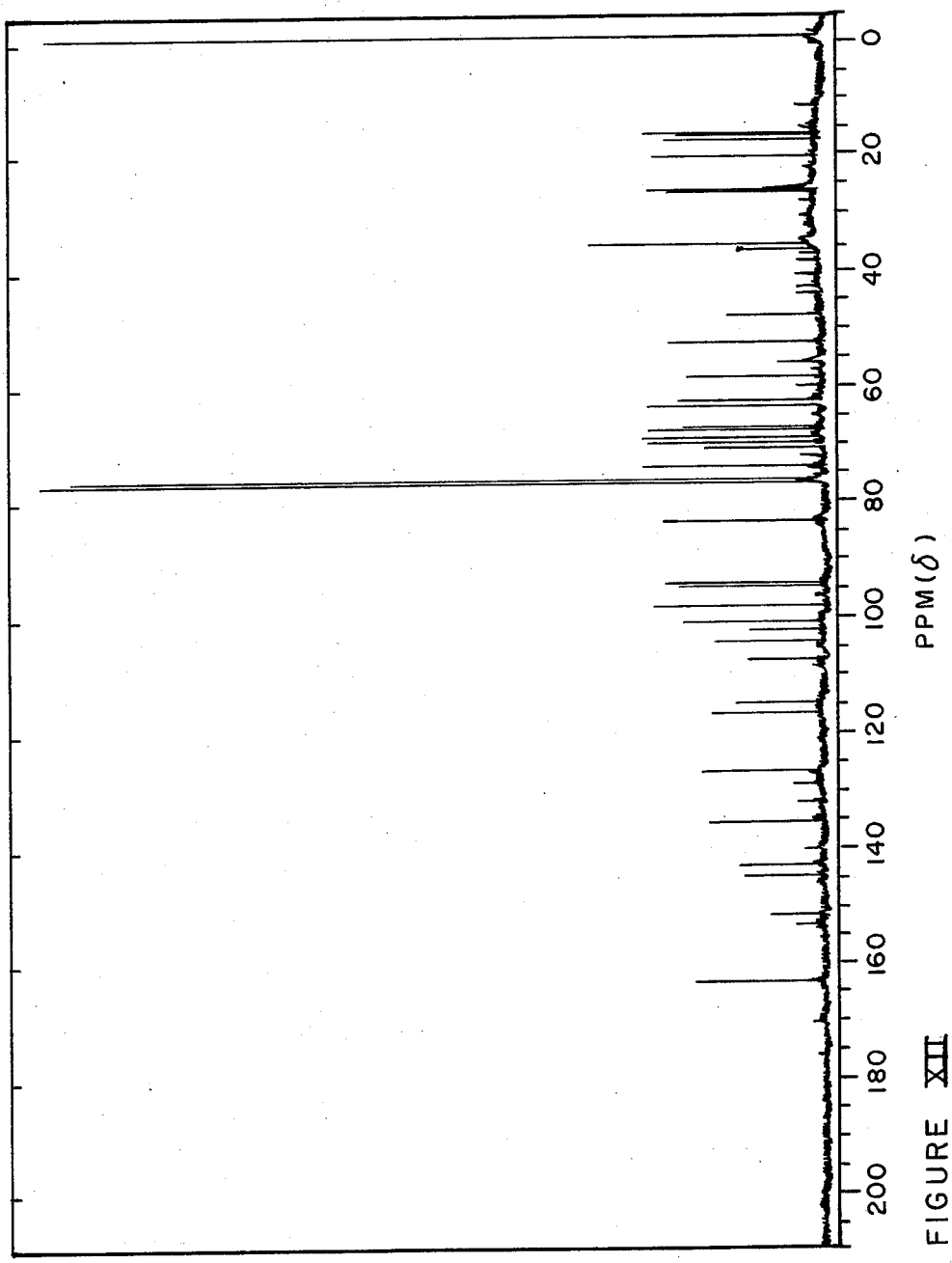

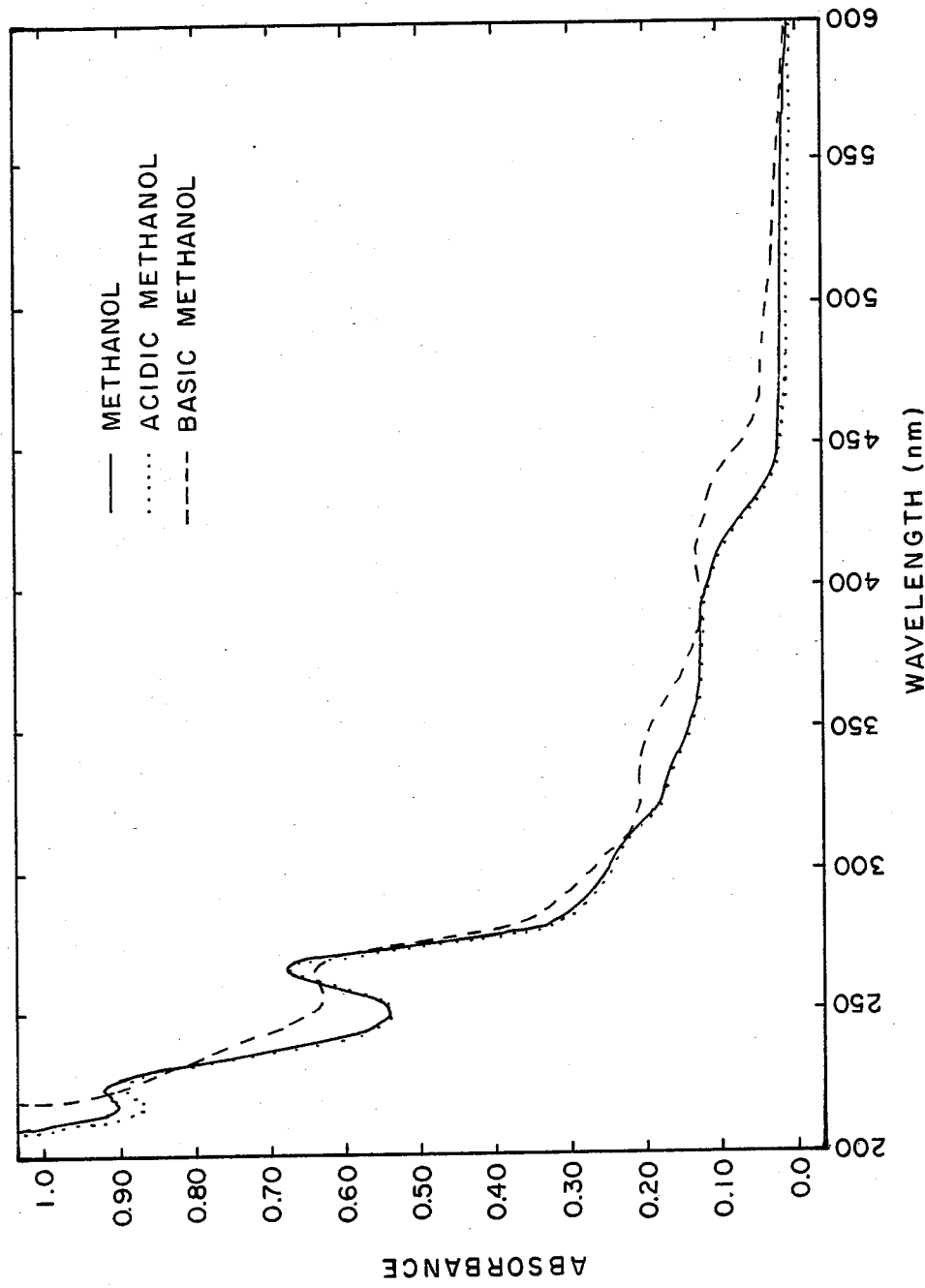
FIGURE XIII

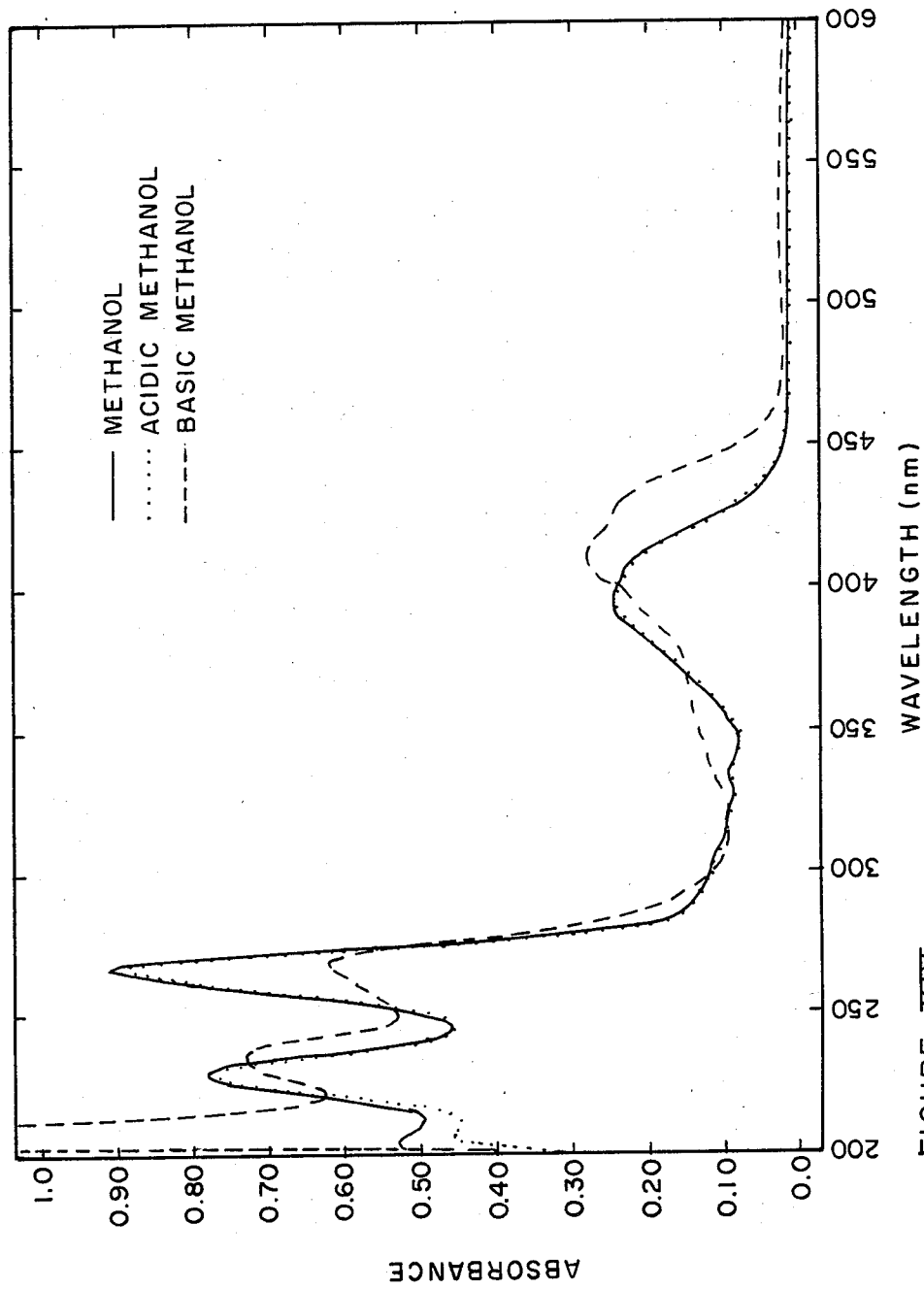
FIGURE XIV

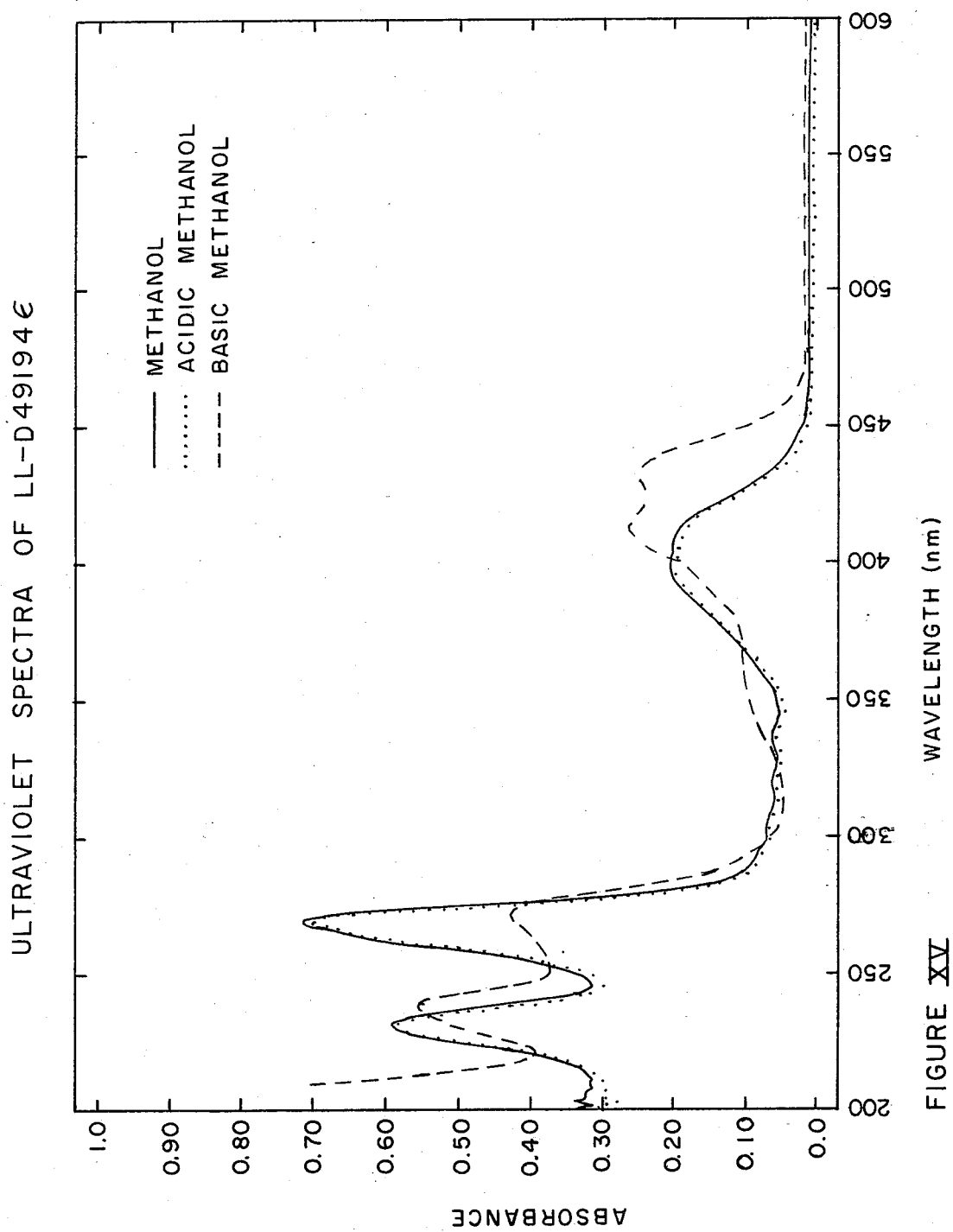

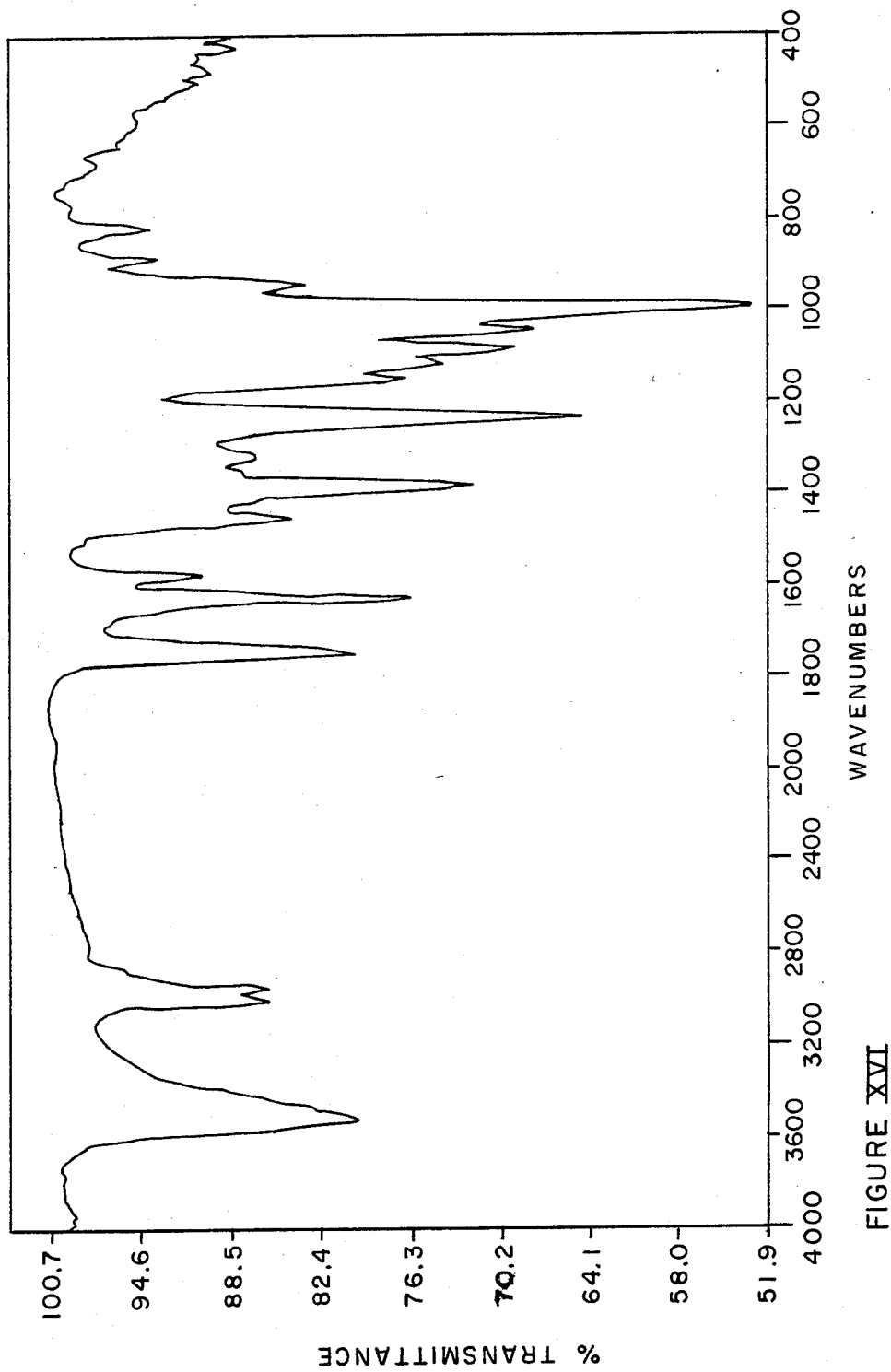

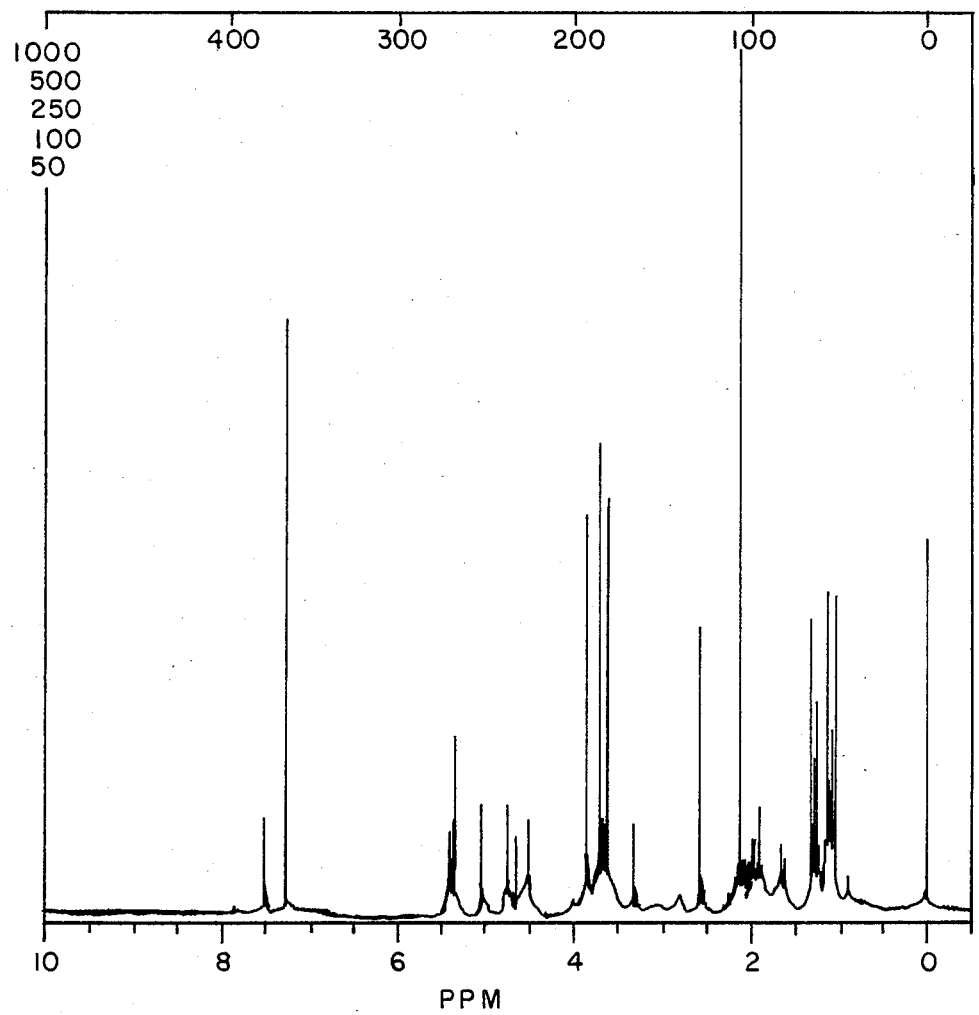
FIGURE XVII

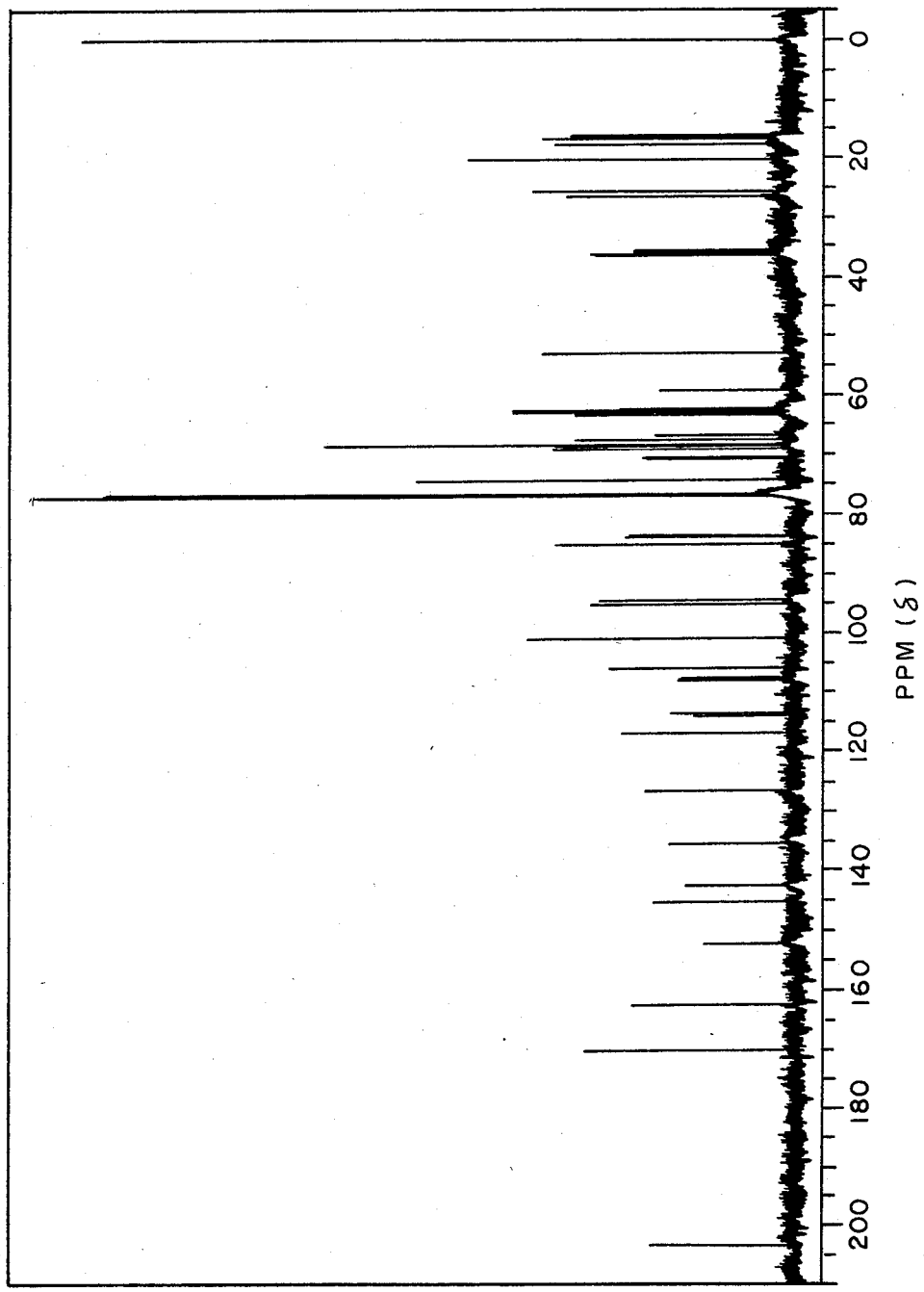
FIGURE XVIII

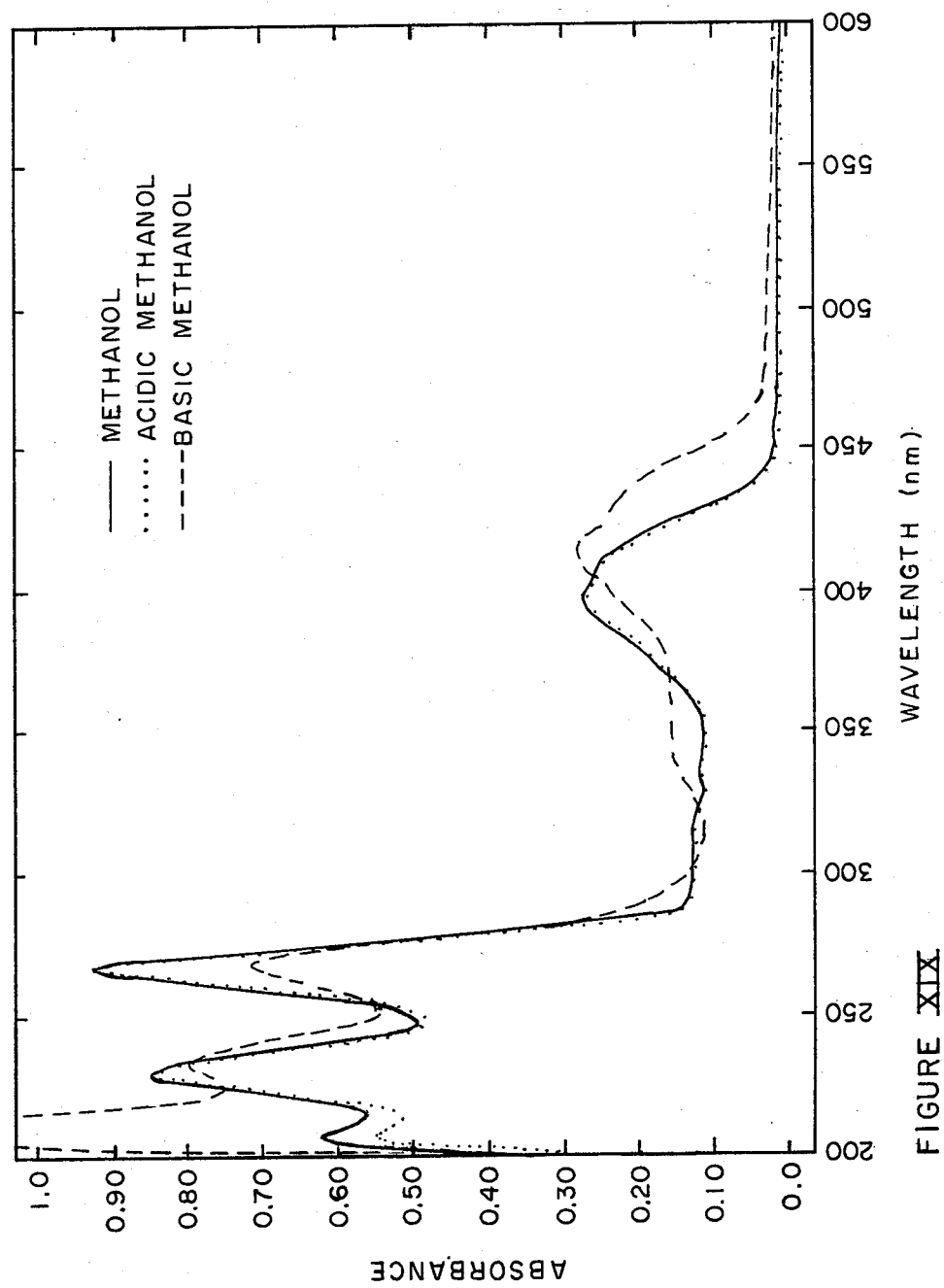

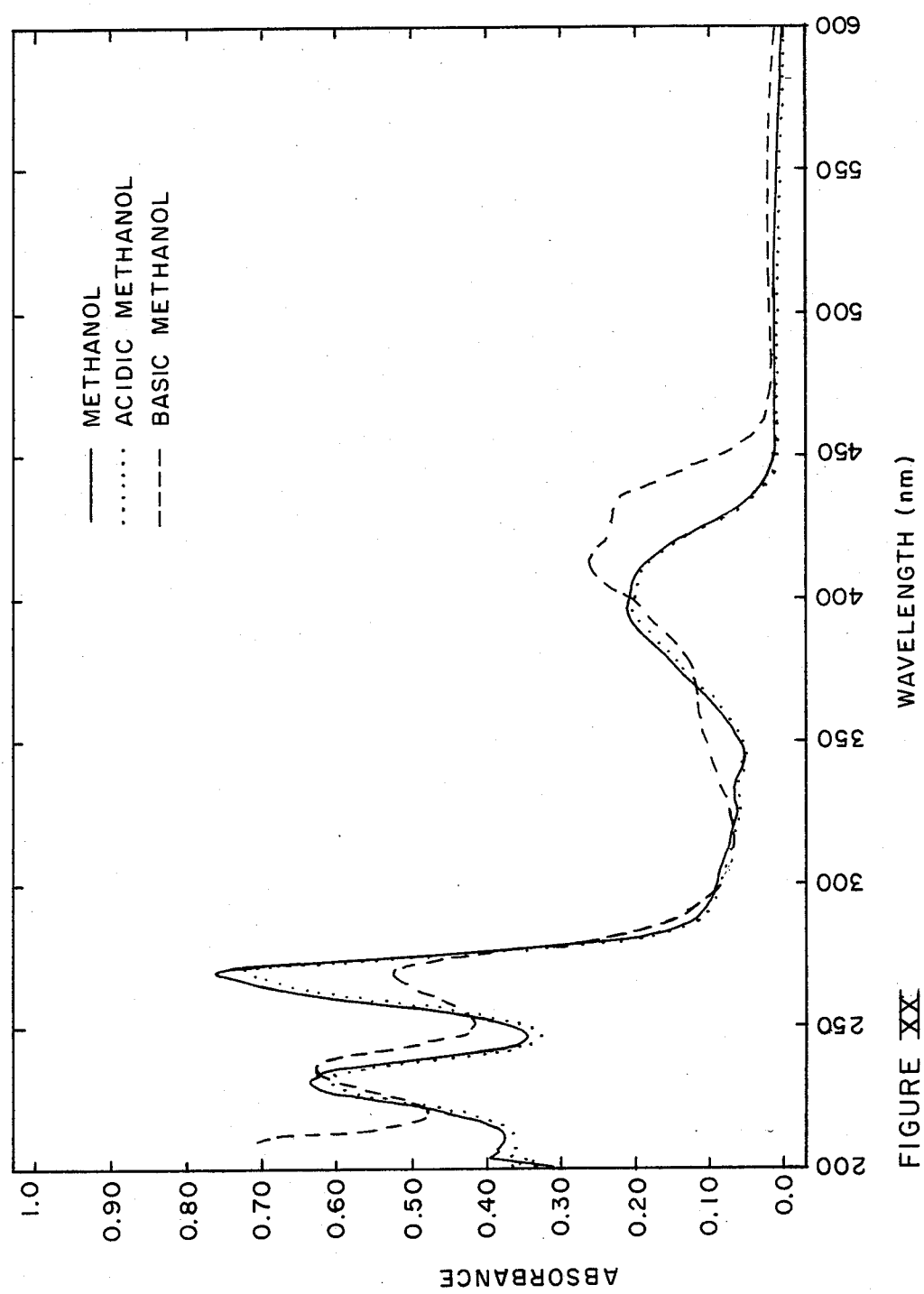

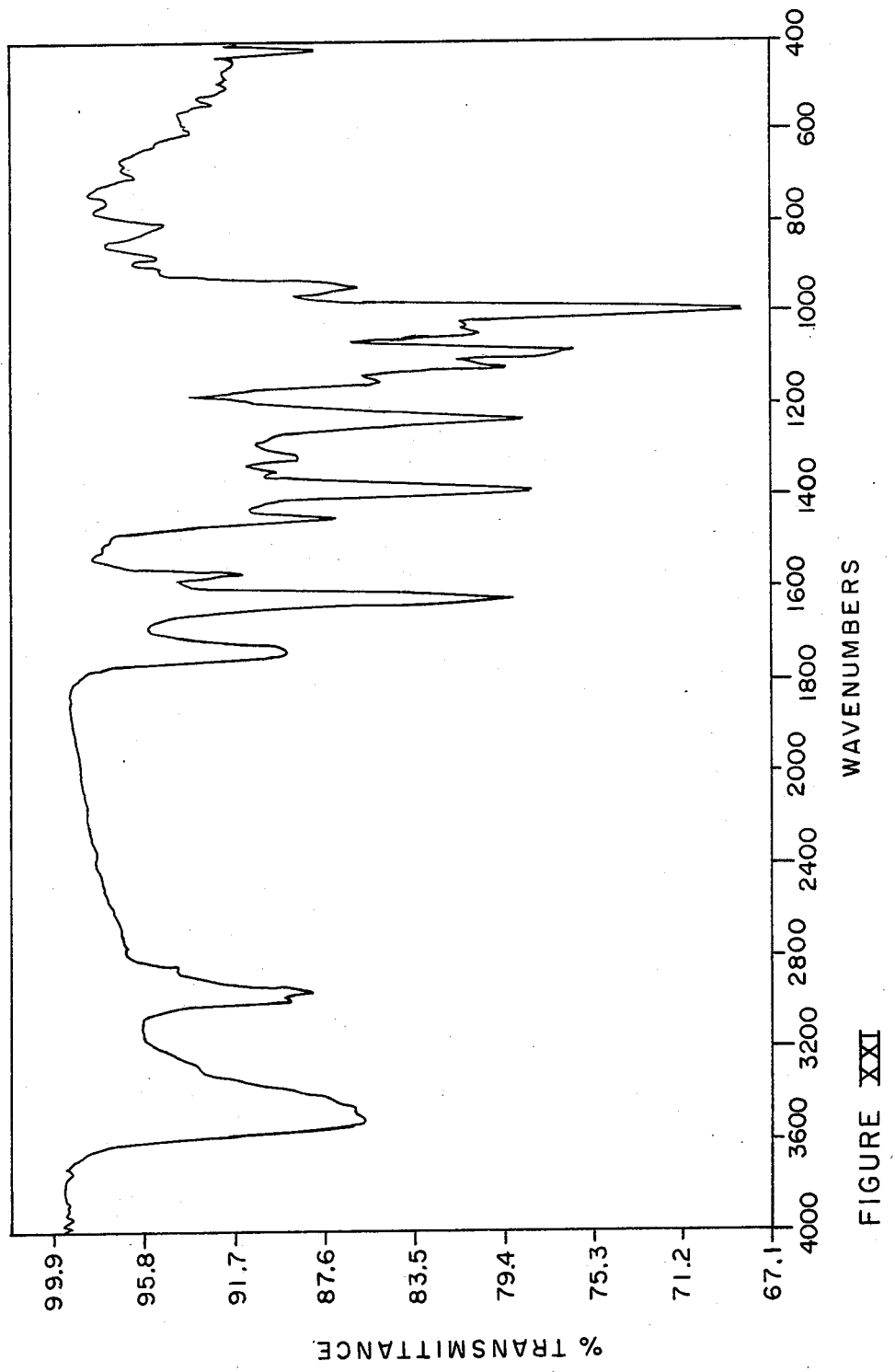
FIGURE XXI

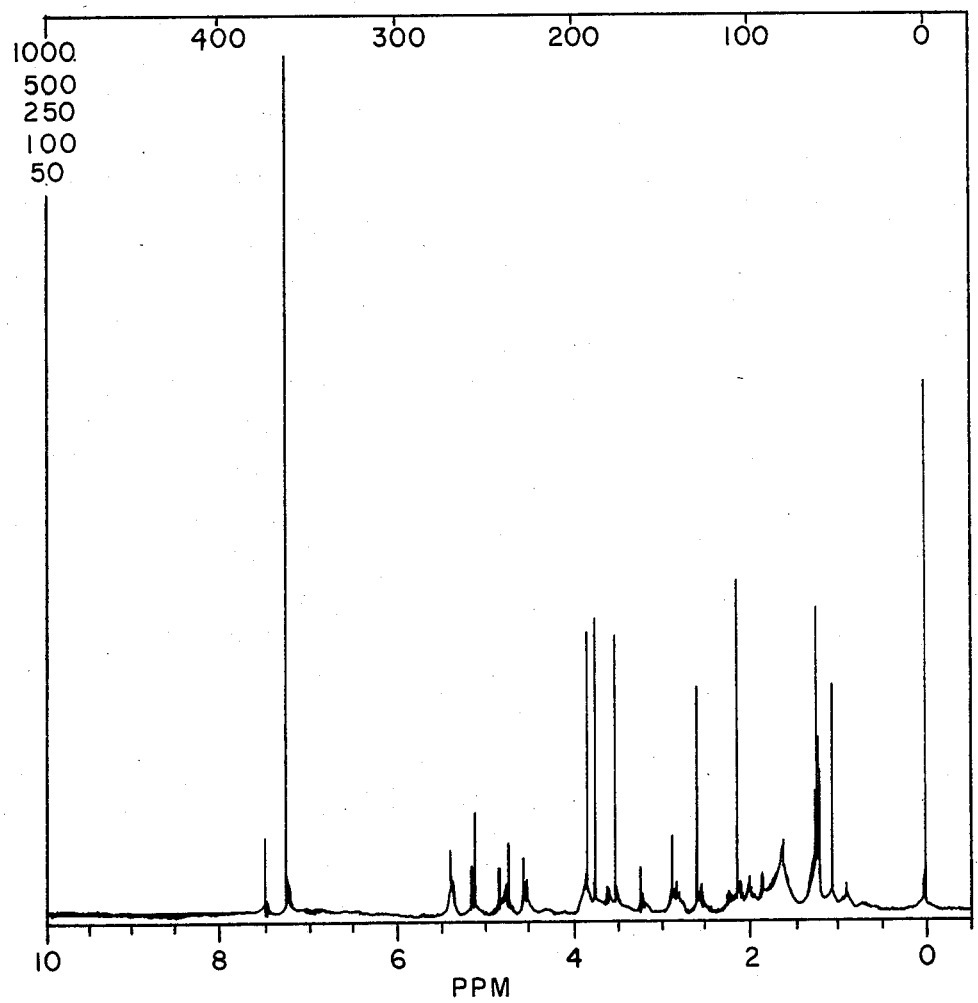
FIGURE XXII

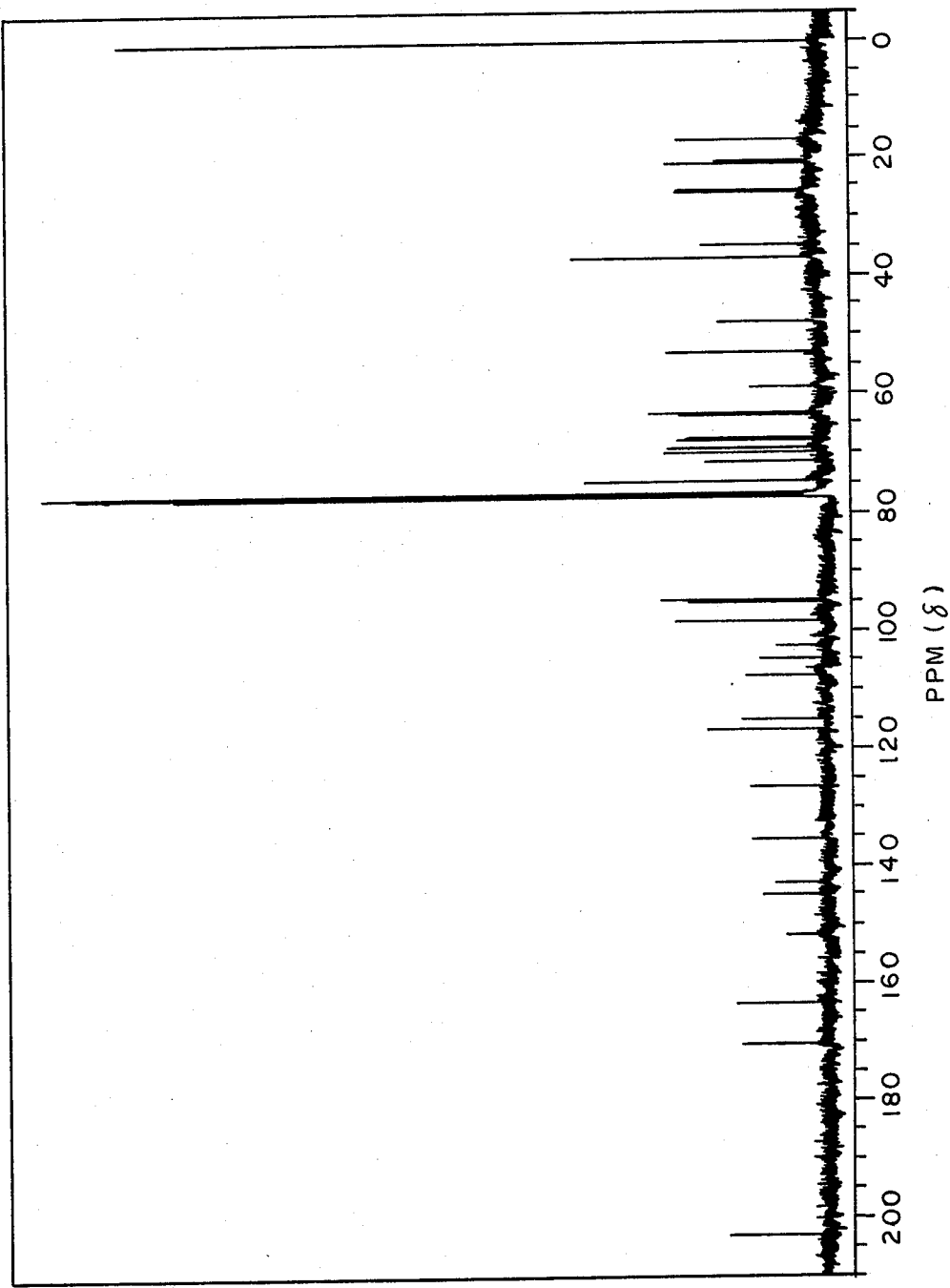
FIGURE XXIII

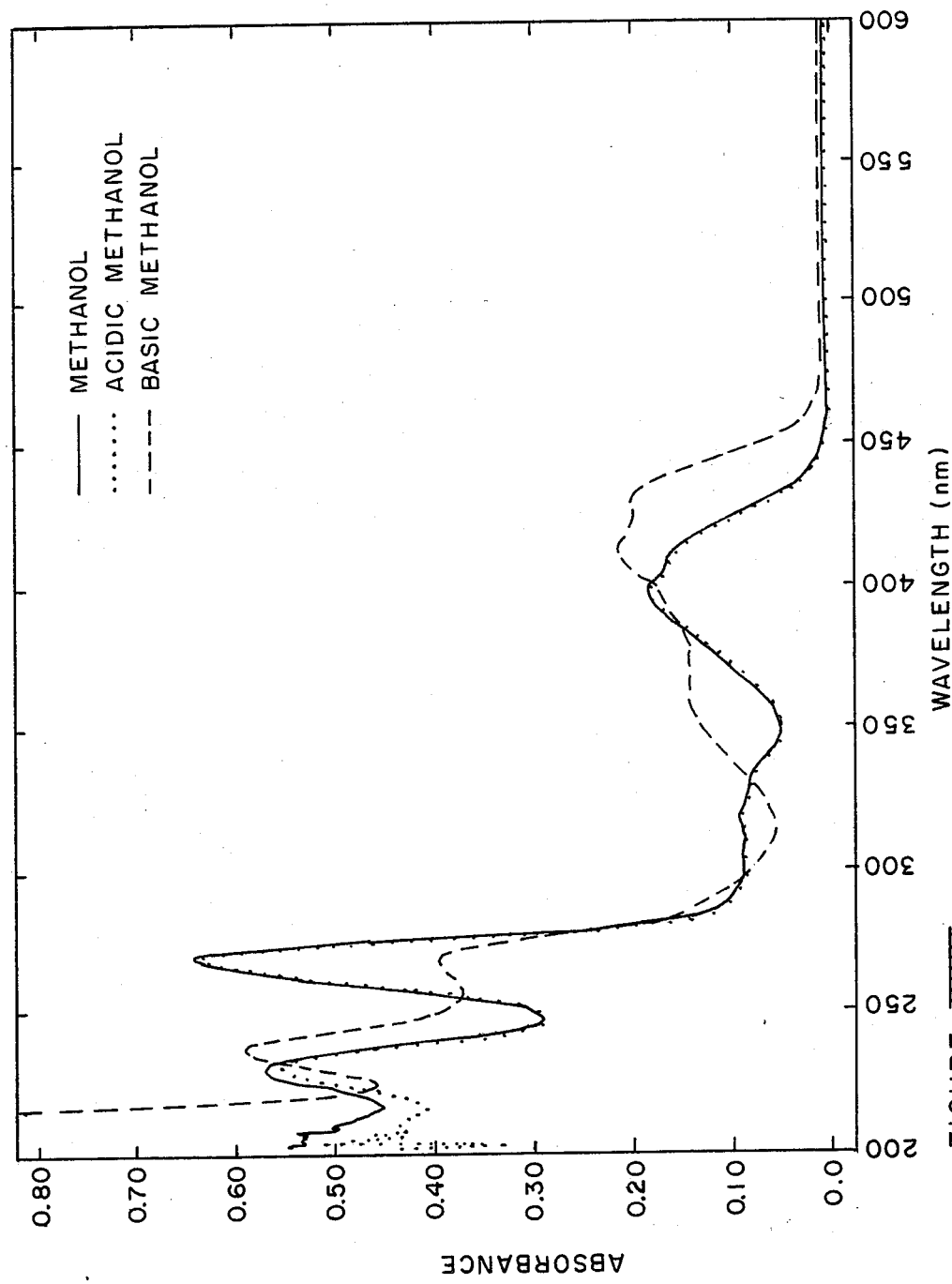

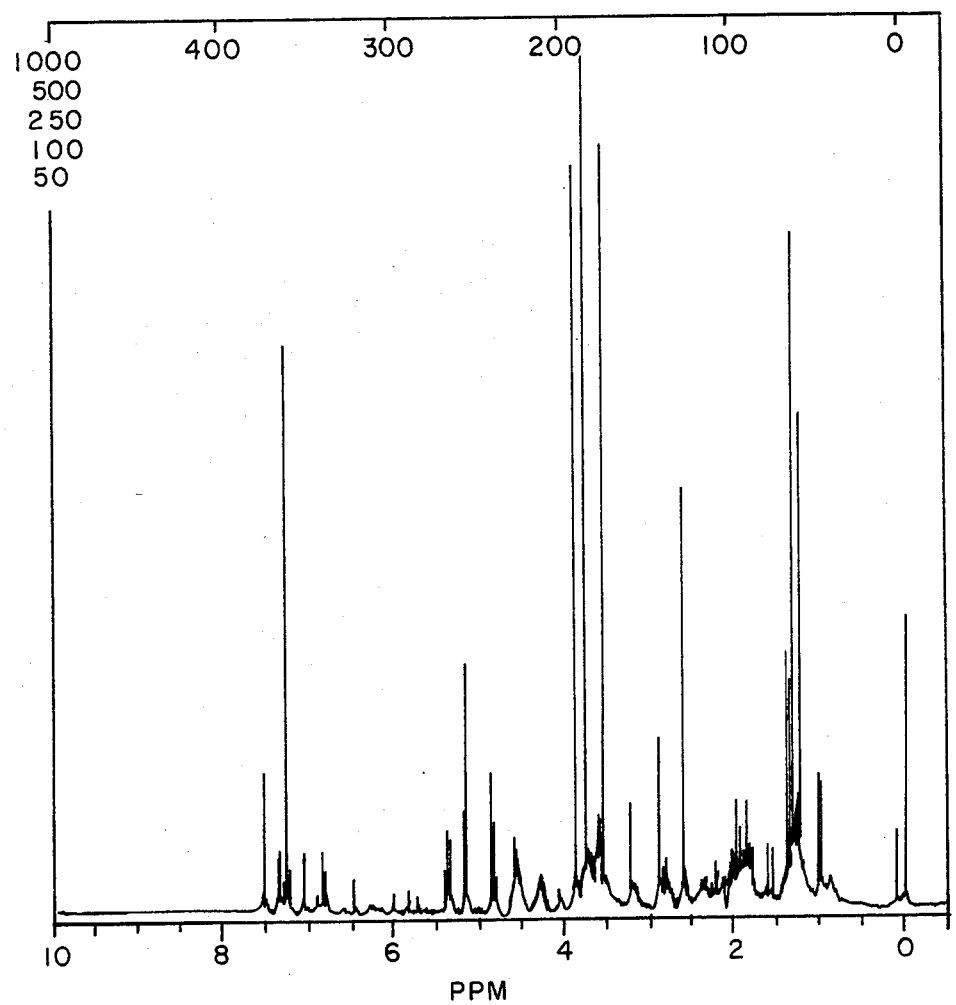
FIGURE XXV

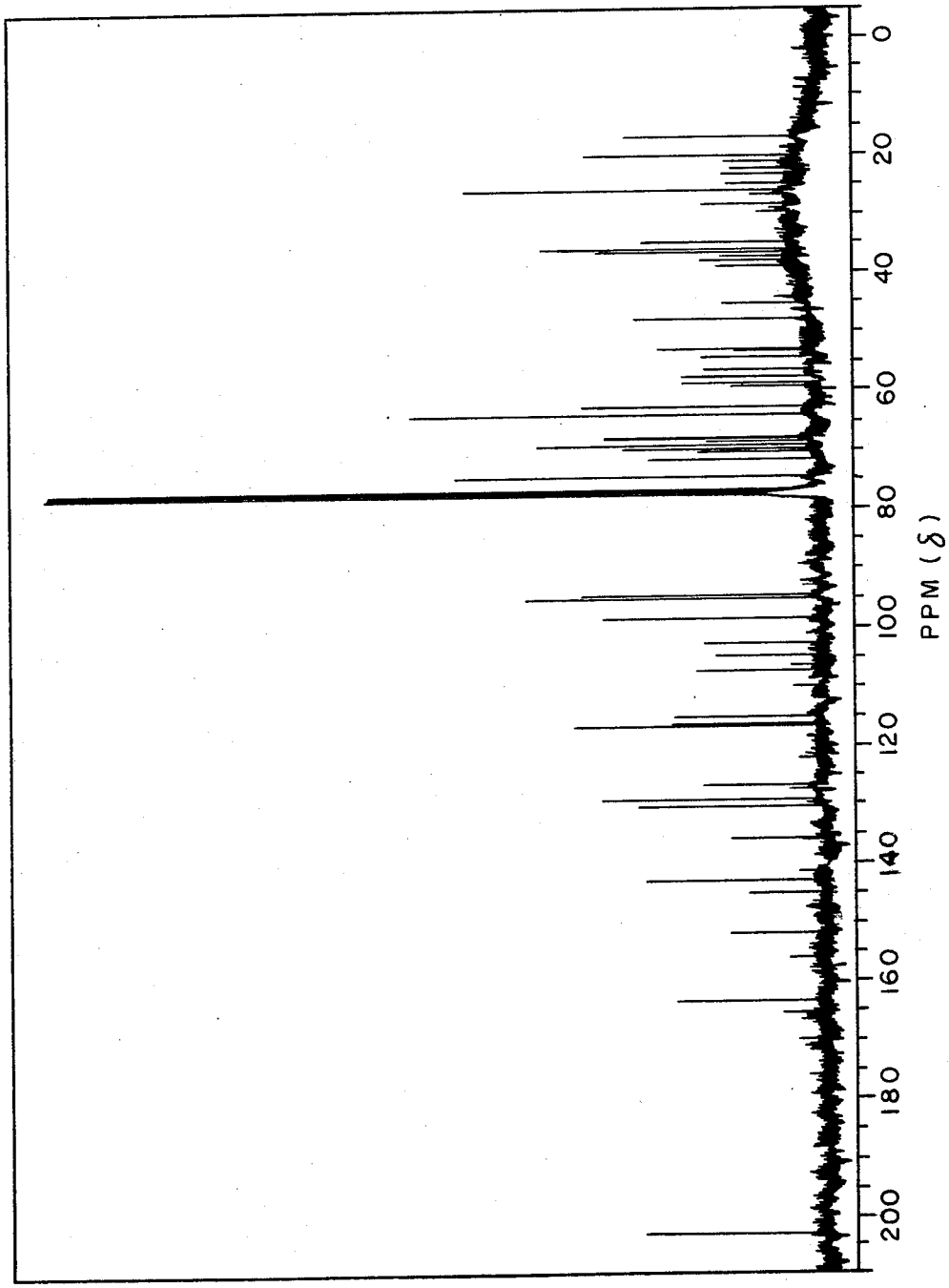
FIGURE XXVI

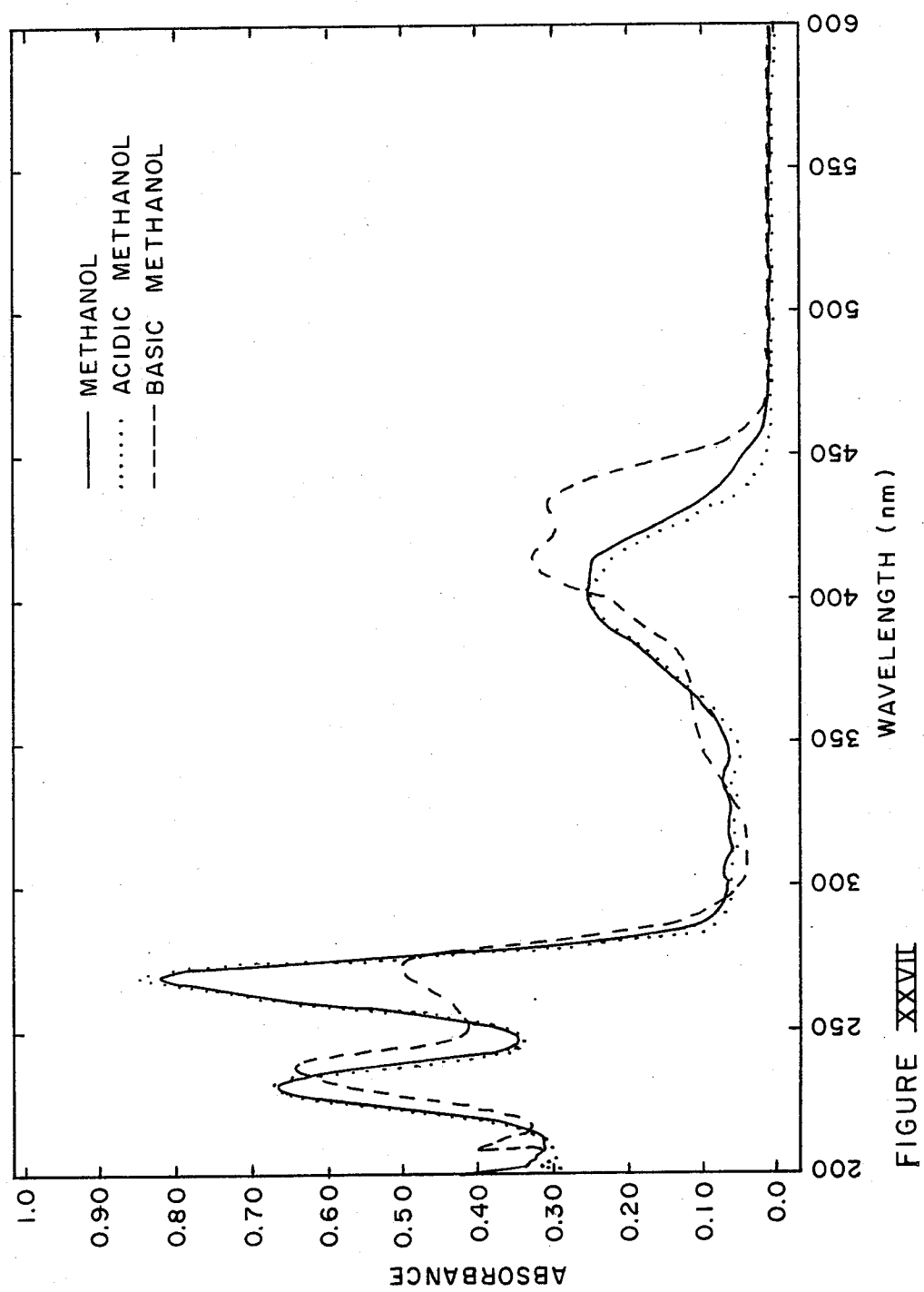

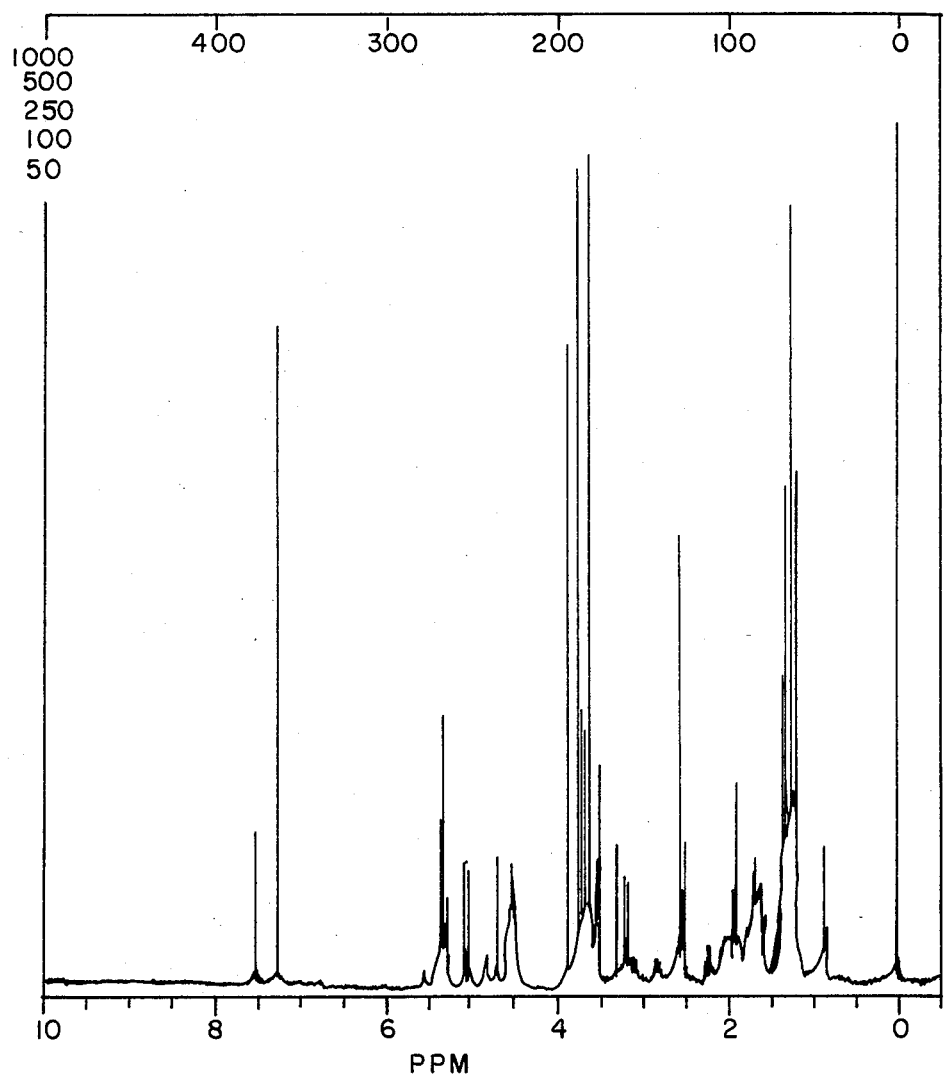
FIGURE XXVIII

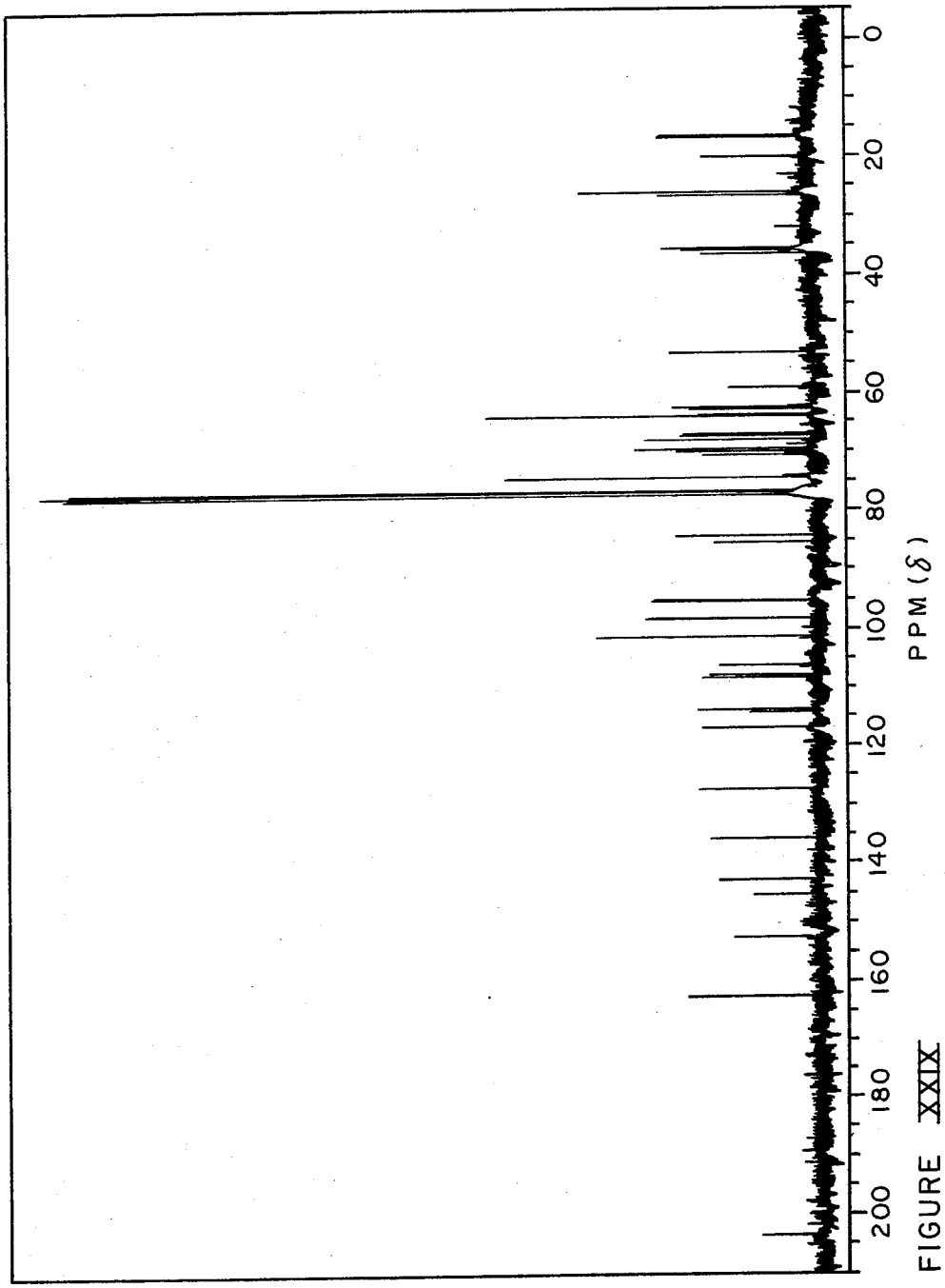
FIGURE XXIX

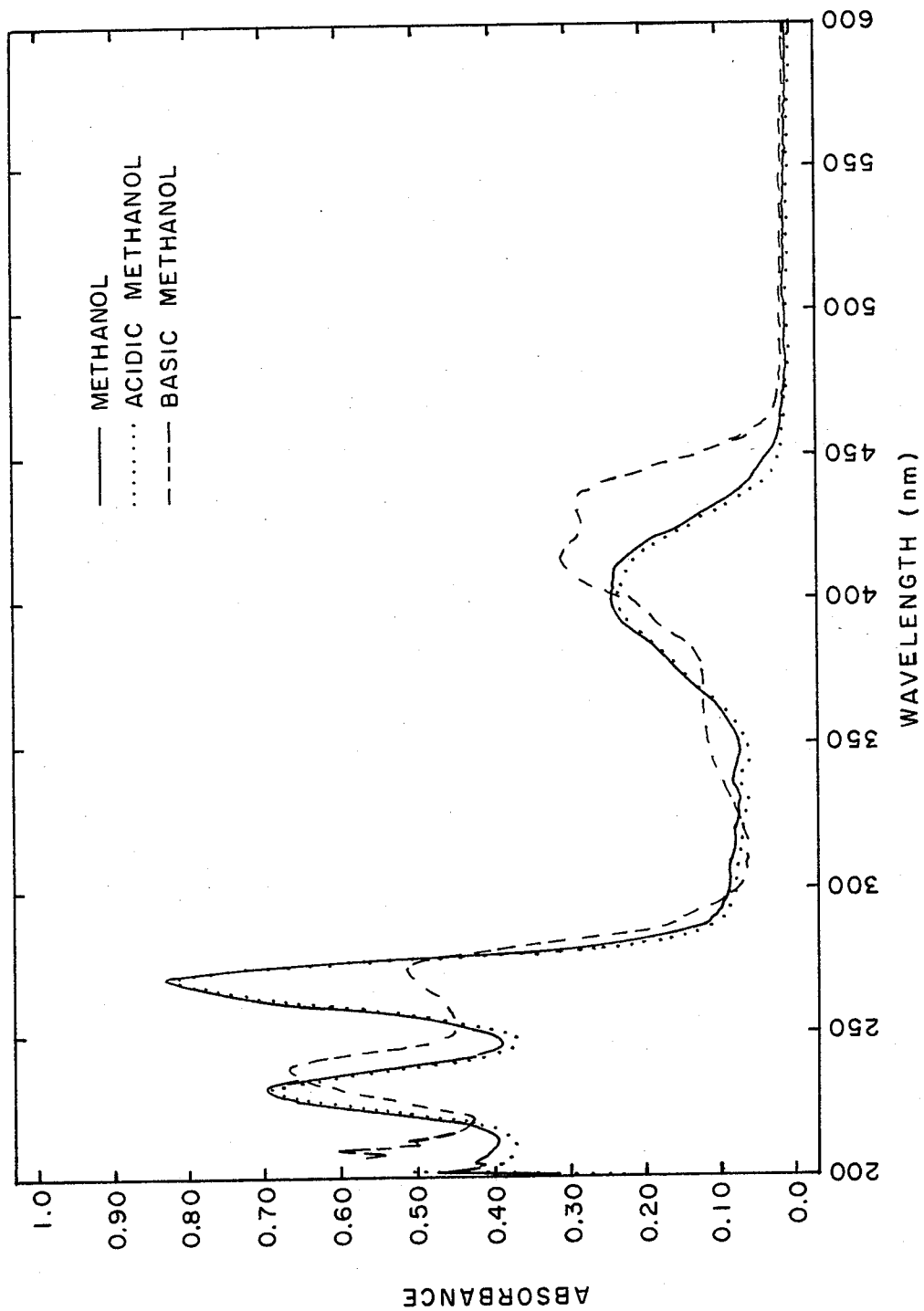
FIGURE XXX

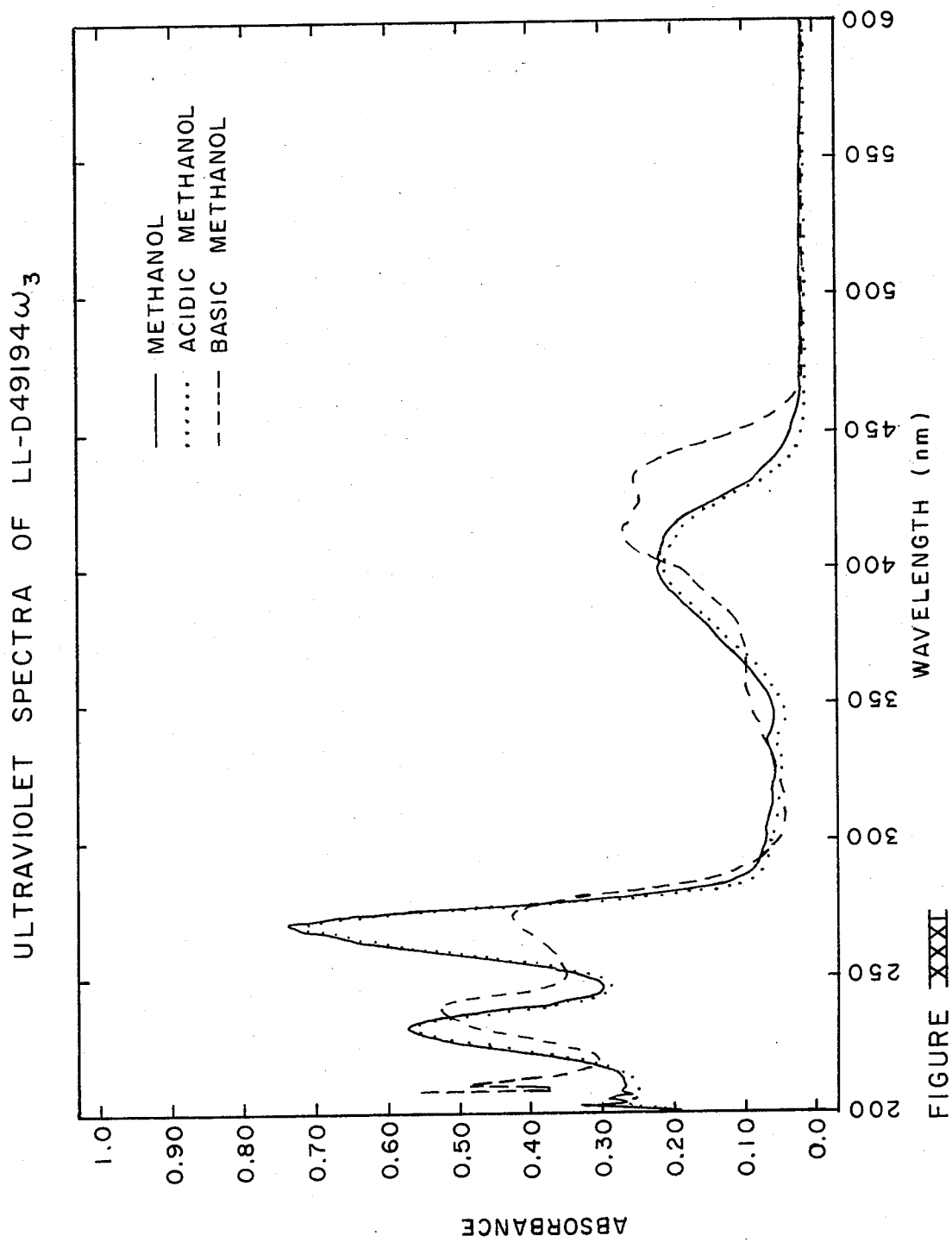

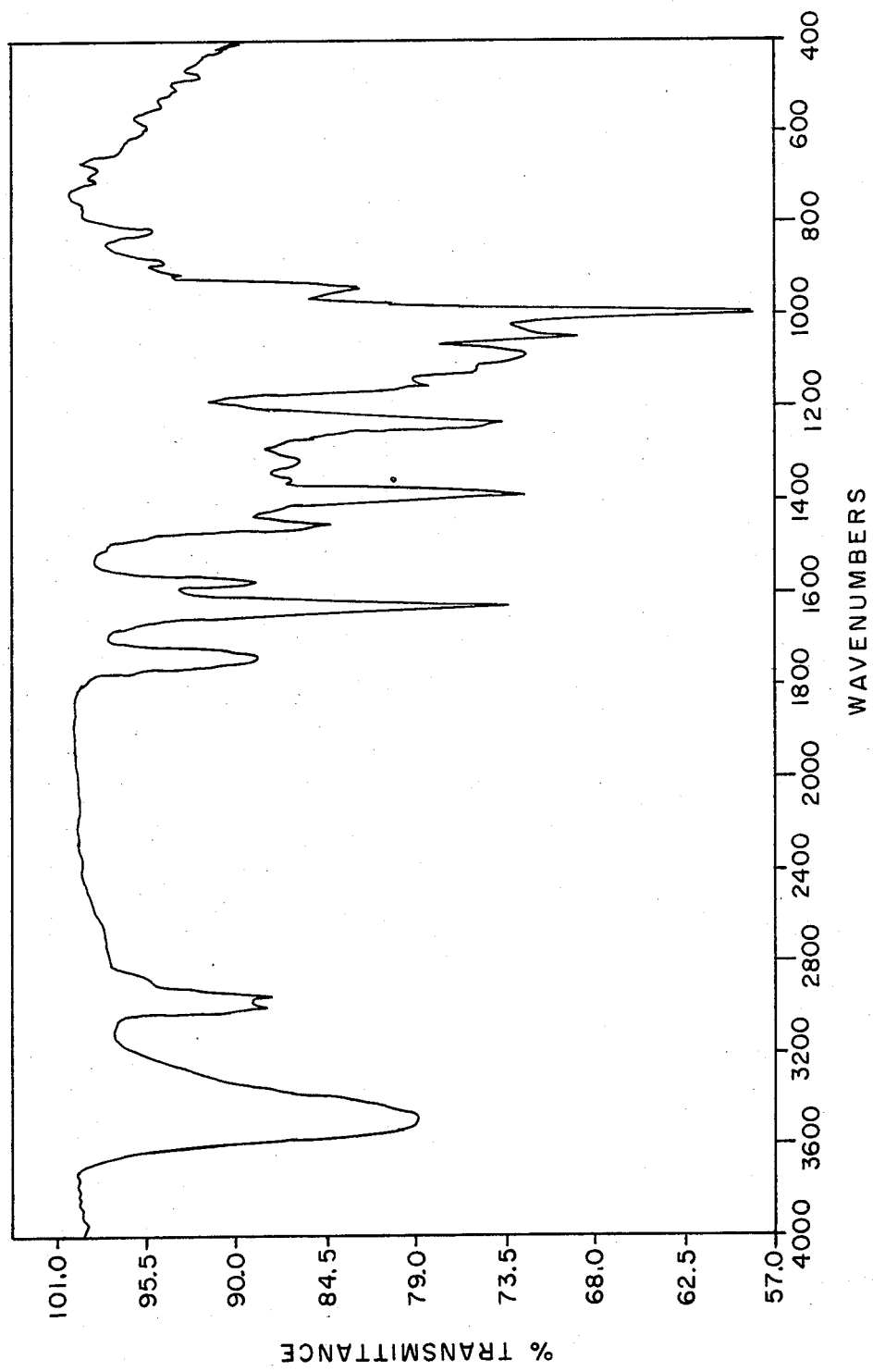

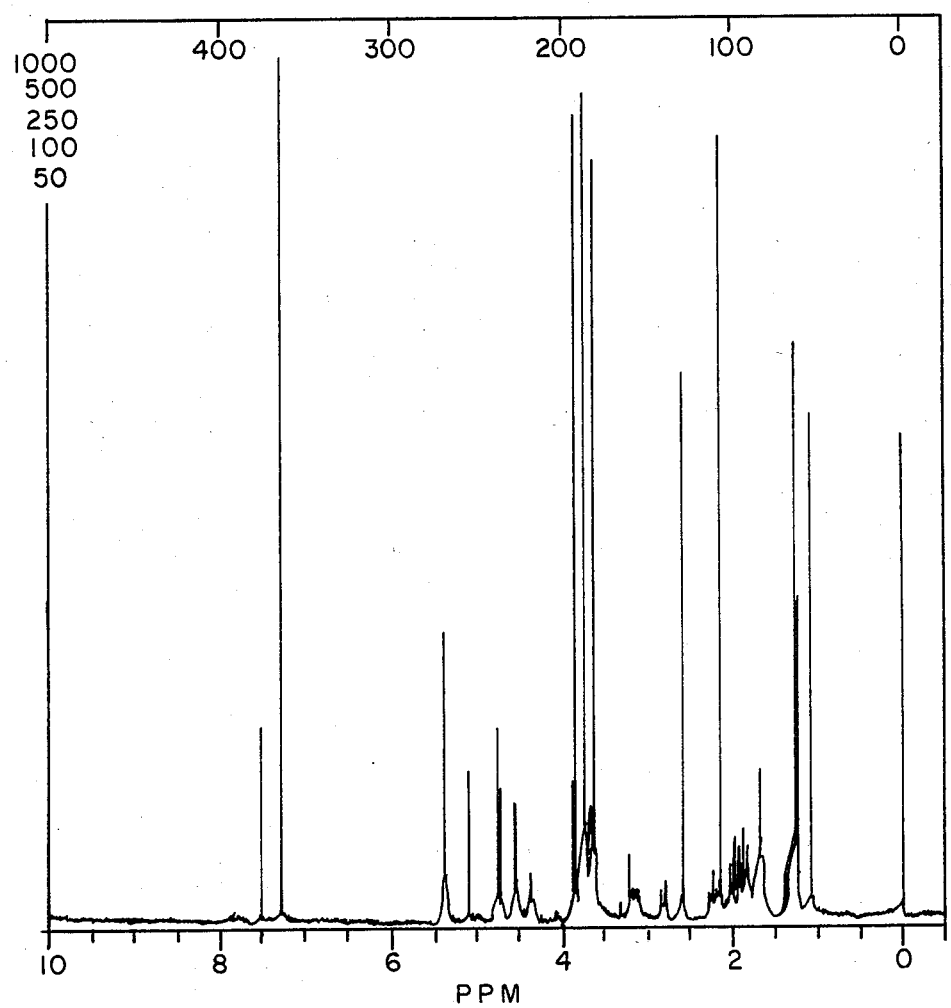
FIGURE XXXIII

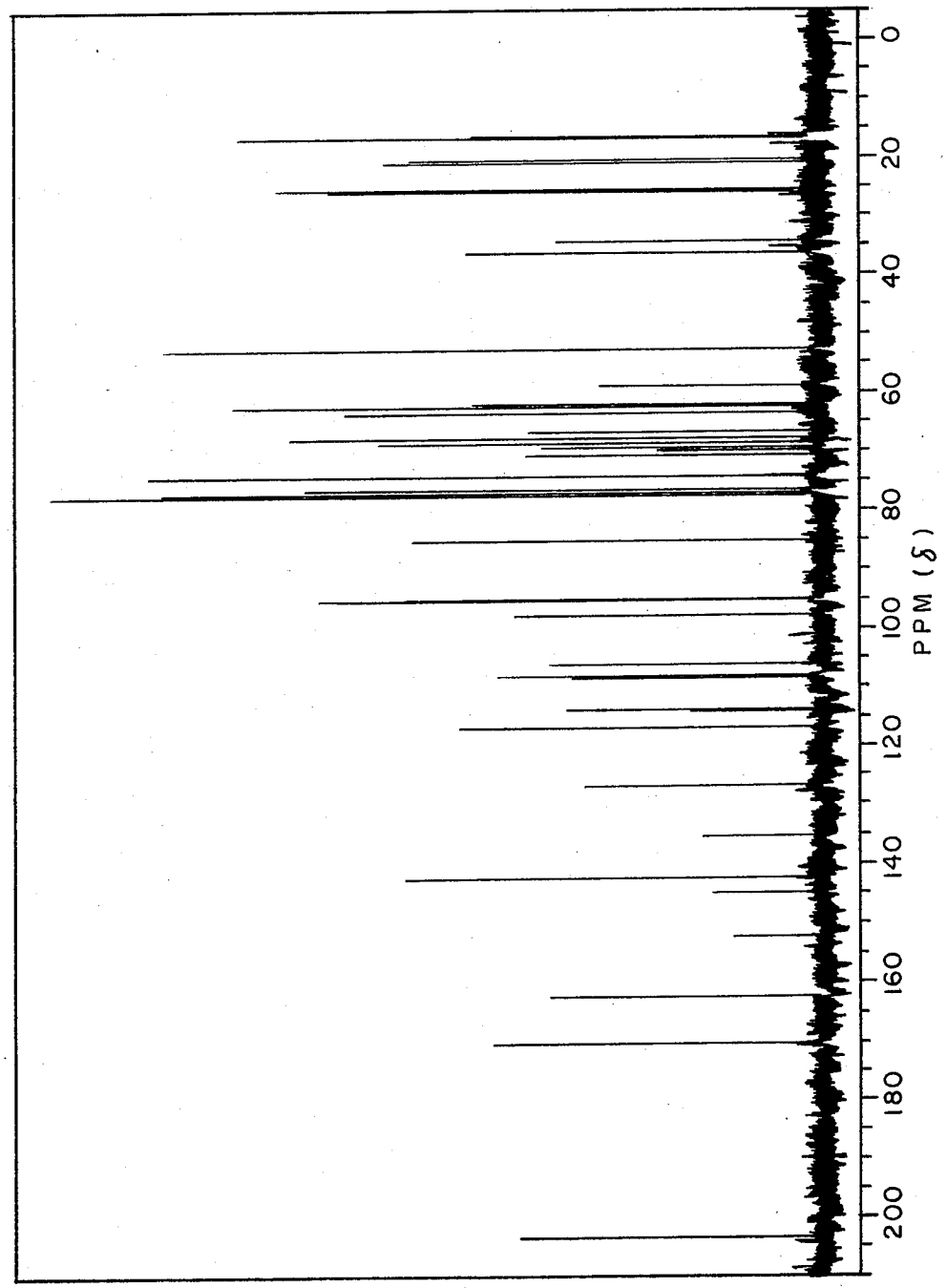
FIGURE XXXIV

ANTITUMOR AGENTS LL-D49194$\alpha_1$, LL-D49194$\beta_1$, LL-D49194$\beta_2$, LL-D49194$\beta_3$, LL-D49194$\gamma$, LL-D49194$\delta$, LL-D49194$\epsilon$, LL-D49194$\zeta$, LL-D49194$\eta$, LL-D49194$\omega_1$, LL-D49194$\omega_2$, AND LL-D49194$\omega_3$

CROSS REFERENCE TO RELATED APPLICATION

This application is a continuation-in-part of our co-pending application Ser. No. 596,499, filed Apr. 4, 1984 and now abandoned.

SUMMARY OF THE INVENTION

The invention relates to new antibacterial and antitumor agents designated LL-D49194$\alpha_1$, LL-D49194$\beta_1$, LL-D49194$\beta_2$, LL-D49194$\beta_3$, LL-D49194$\gamma$, LL-D49194$\delta$, LL-D49194$\epsilon$, LL-D49194$\zeta$, LL-D49194$\eta$, LL-D49194$\omega_1$, LL-D49194$\omega_2$, and LL-D49194$\omega_3$; to their production by fermentation, to methods for their recovery and concentration from crude solutions and to processes for their purification. The present invention includes within its scope the antibacterial and antitumor agents in dilute form, as crude concentrates and in pure form.

The LL-D49194 antibiotics of this invention are closely related compounds. The twelve antibiotics are initially recovered from the fermentation as a mixture. The ratio of components in the LL-D49194 complex will vary, depending upon the fermentation conditions used. In general, however, LL-D49194$\alpha_1$ and LL-D49194$\beta_1$ are the major components, together accounting for approximately 90% of the complex. The other ten antibiotics are minor components, together accounting for approximately 10% of the complex. The twelve components are separated and isolated as individual compounds as hereinafter described.

The LL-D49194 antibiotics are closely related to the recently discovered trioxacarcins [The J. of Antibiotics, Vol. 12, December, 1981, pp 1520–1530; European Patent Application No. 0029309 (filed 10-27-80); Chemical Abstracts 96, 200027h]. All of the LL-D49194 components can be separated from trioxacarcins A, B and C by high performance liquid chromatography. In addition, the $^1$HNMR and $^{13}$CNMR spectral data of LL-D49194$\alpha_1$, $\beta_1$, and $\beta_2$ clearly distinguish them from the trioxacarcins.

While the structures for all of the individual components of the LL-D49194 complex have not been fully elucidated, structures for the $\alpha_1$, $\beta_1$, $\beta_2$, $\epsilon$, $\eta$, $\beta_3$, $\omega_1$ and $\omega_3$ components are postulated below.

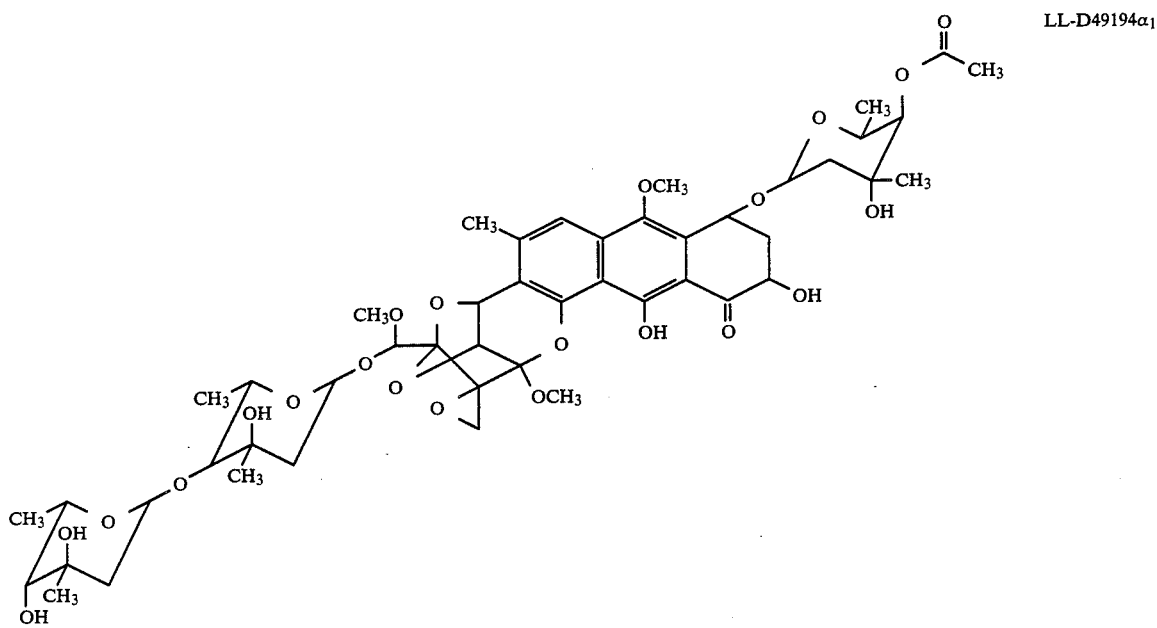

-continued
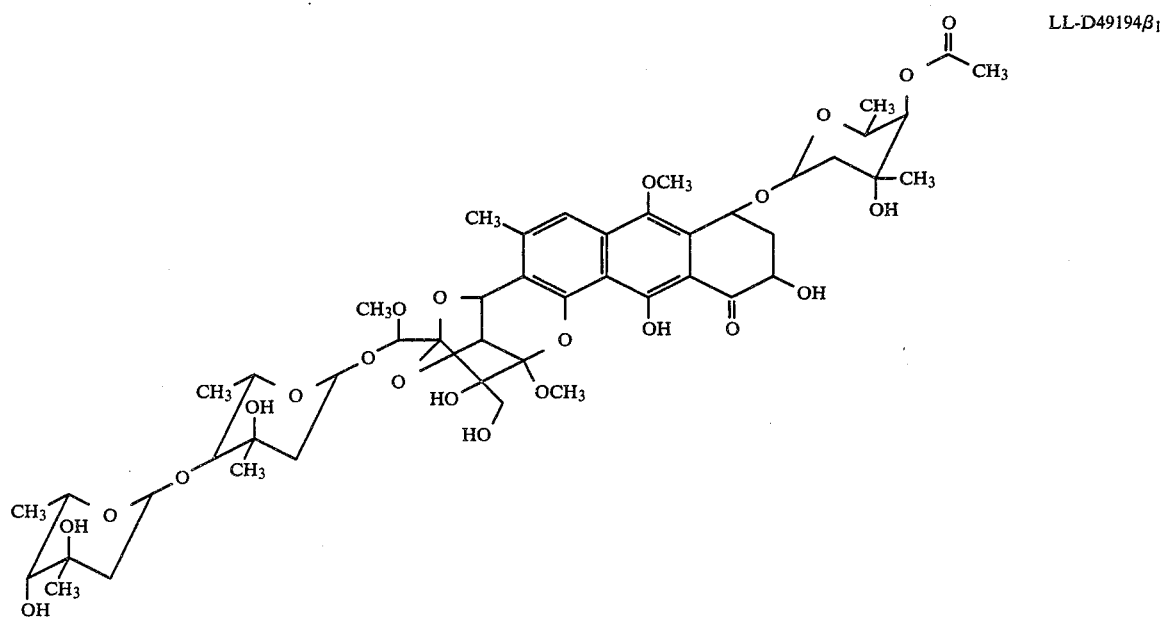
LL-D49194β₁
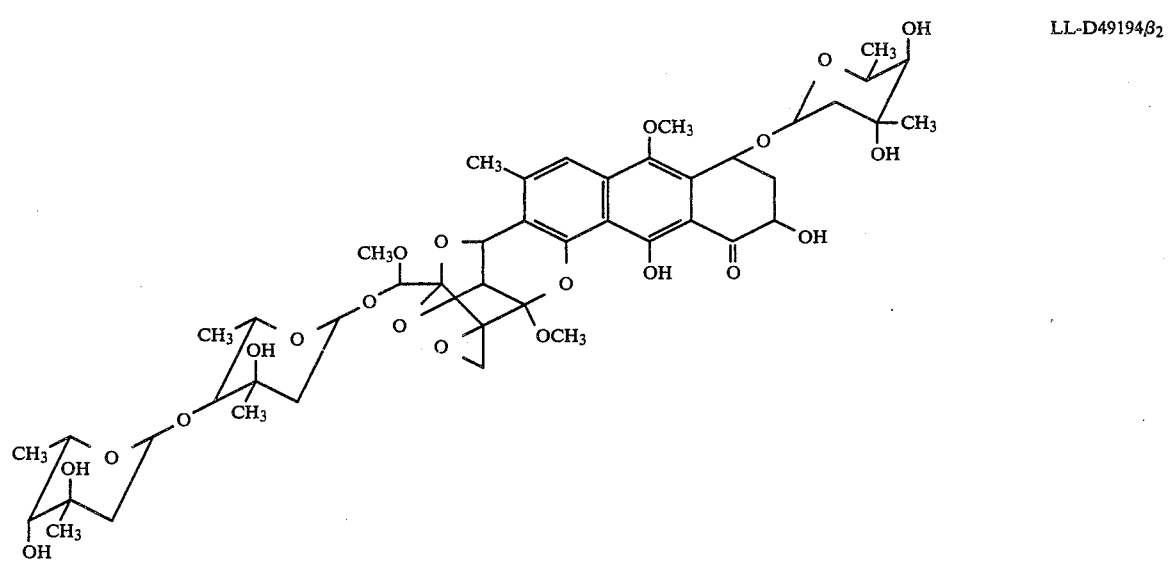
LL-D49194β₂

-continued
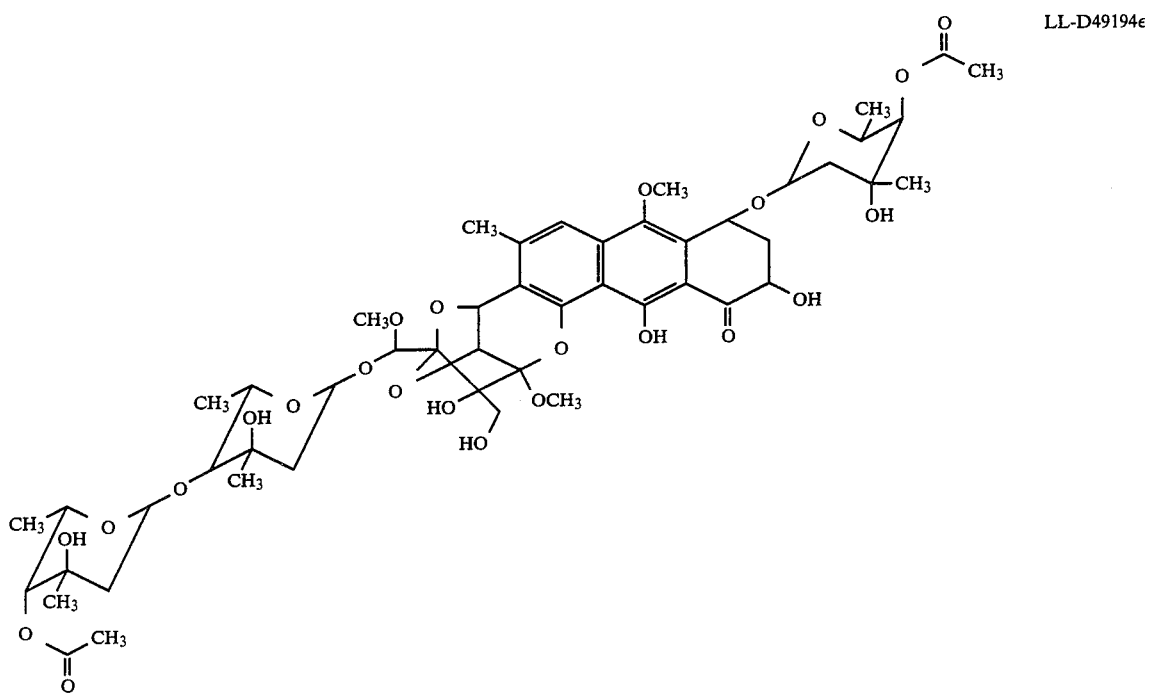
LL-D49194ε
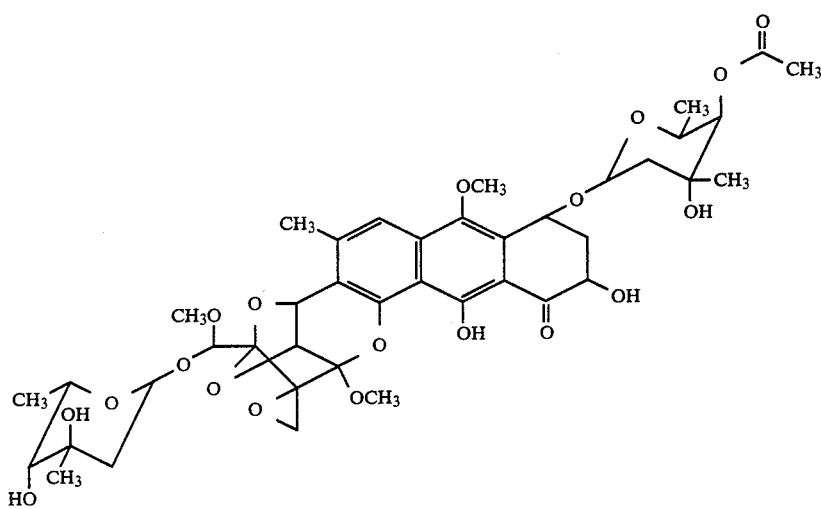
LL-D49194η
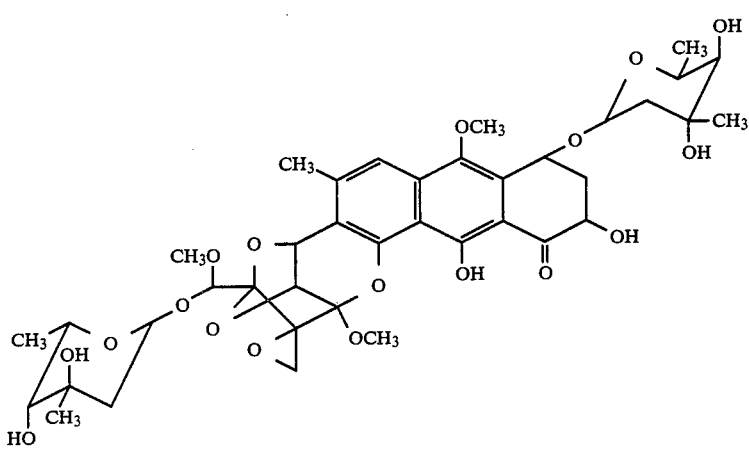
LL-D49194β₃

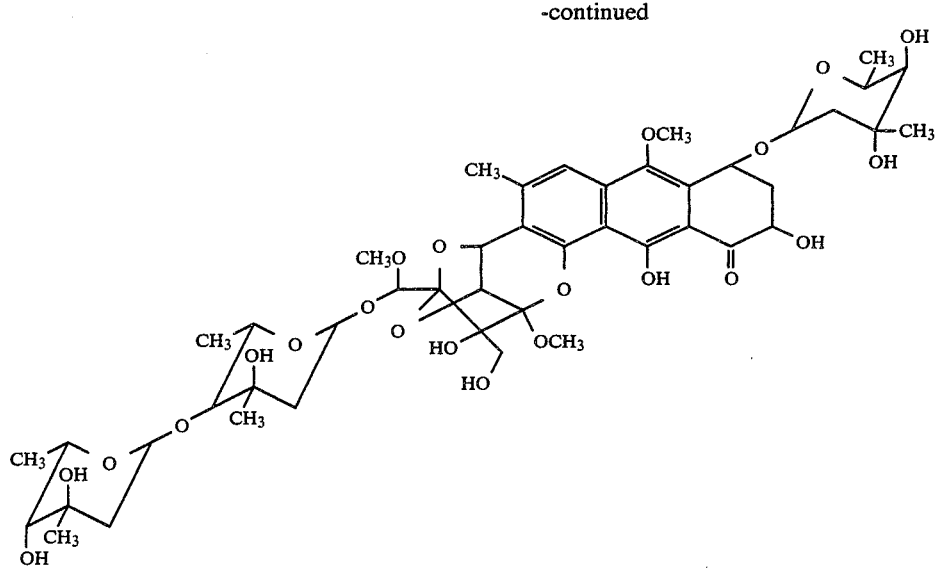

LL-D49194ω₁

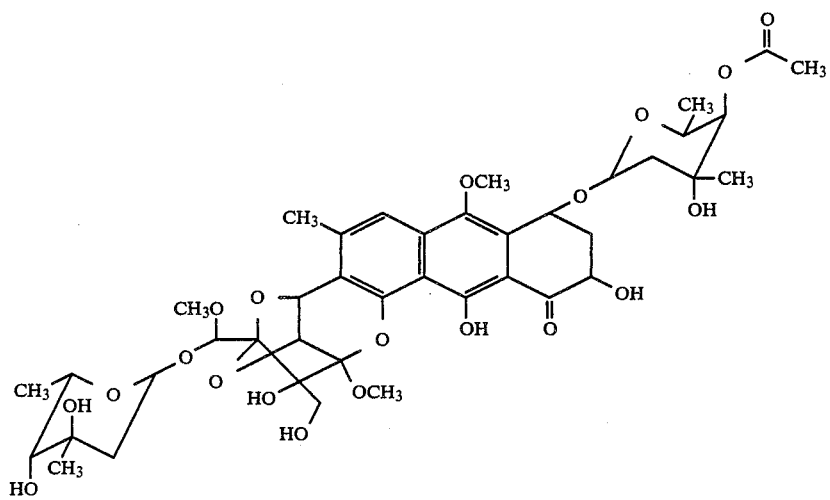

LL-D49194ω₃

The physico-chemical characteristics of the individual LL-D49194 antibiotics of this invention are described below:

LL-D49194α₁

(1) Molecular weight: 992 (FDMS);
(2) Molecular formula: $C_{48}H_{64}O_{22}$ (high resolution FDMS);
(3) Melting point: 173°–176° C. (dec.);
(4) Specific rotation: $[\alpha]_D^{26} = 0°(0.57\%$, ethanol);
(5) Ultraviolet absorption spectra: as shown in FIG. I (ethanol; 0.1N hydrochloric acid; 0.1N sodium hydroxide);
(6) Infrared absorption spectrum: as shown in FIG. II (KBr disc);
(7) Proton magnetic resonance spectrum: as shown in FIG. III (300 MHz, $CDCl_3$);
(8) Carbon-13 magnetic resonance spectrum: as shown in FIG. IV (75.43 MHz, $CDCl_3$, ppm from TMS). Significant peaks as listed below:
16.5; 16.9; 17.6; 20.4; 20.9; 25.7; 26.2; 26.7; 35.6; 36.7; 47.8; 52.8; 58.8; 62.7; 62.9; 63.9; 67.4; 67.9; 68.8; 69.0; 69.1; 69.2; 70.1; 71.3; 74.3; 74.4; 83.9; 94.2; 94.8; 97.9; 101.0; 102.3; 104.3; 107.3; 114.8; 114.9; 116.7; 126.5; 135.4; 142.9; 144.8; 151.5; 163.2; 170.3; 202.8.

(9) Releases methyl α-L-axenoside and methyl β-L-axenoside upon treatment with dilute methanolic hydrochloric acid.

LL-D49194β₁

(1) Molecular weight: 1010 (FDMS);
(2) Molecular formula: $C_{48}H_{66}O_{23}$(high resolution FDMS);
(3) Melting point: 163°–167° C. (dec.);
(4) Specific rotation:
$[\alpha]_D^{26} = -51 \pm 10°(0.137\%$, ethanol)
$[\alpha]_D^{26} = -119 \pm 10°(0.135\%$, chloroform);
(5) Ultraviolet absorption spectra: as shown in FIG. V (ethanol; 0.1N hydrochloric acid; 0.1N sodium hydroxide);
(6) Infrared absorption spectrum: as shown in FIG. VI (KBr disc);
(7) Proton magnetic resonance spectrum: as shown in FIG. VII (300 MHz, $CDCl_3$);
(8) Carbon-13 magnetic resonance spectrum: as shown in FIG. VIII (75.43 MHz, $CDCl_3$, ppm from TMS). Significant peaks as listed below:

16.5; 16.9; 17.6; 20.1; 20.8; 25.8; 26.3; 26.8; 35.7; 35.8; 36.7; 36.8; 53.0; 58.7; 62.3; 62.7; 62.9; 63.9; 67.1; 67.9; 68.8; 69.3; 69.4; 70.1; 70.7; 74.3; 74.5; 84.0; 85.1; 94.9; 95.2; 97.7; 101.0; 106.0; 107.9; 108.3; 113.6; 114.1; 116.8; 126.8; 135.5; 142.4; 145.1; 152.3; 162.4; 170.3; 203.6.

(9) Releases methyl α-L-axenoside and methyl β-L-axenoside upon treatment with dilute methanolic hydrochloric acid.

LL-D49194β$_2$ (1) Specific rotation: $[\alpha]_D^{26} = +40 \pm 6°(0.15\%$, ethanol);

(2) Ultraviolet absorption spectra: as shown in FIG. IX (methanol; 0.1N hydrochloric acid; 0.1N sodium hydroxide);

(3) Infrared absorption spectrum: as shown in FIG. X (KBr disc);

(4) Proton magnetic resonance spectrum: as shown in FIG. XI (300 MHz, CDCl$_3$);

(5) Carbon-13 magnetic resonance spectrum: as shown in FIG. XII (75.43 MHz, CDCl$_3$, ppm from TMS). Significant peaks as listed below:

16.5; 16.9; 17.6; 20.3; 26.1; 26.2; 26.7; 35.6; 35.9; 36.6; 47.9; 52.8; 58.7; 62.7; 63.6; 63.9; 67.6; 68.0; 69.0; 69.1; 69.3; 70.1; 70.2; 71.2; 74.2; 74.4; 83.9; 94.2; 94.8; 98.1; 101.0; 102.3; 104.2; 107.4; 114.8; 114.9; 116.6; 126.6; 135.5; 142.9; 144.7; 151.5; 163.2; 202.9.

(6) Releases methyl α-L-axenoside and methyl β-L-axenoside upon treatment with dilute methanolic hydrochloric acid.

LL-D49194γ

Ultraviolet absorption spectra: as shown in FIG. XIII (methanol, acidic methanol, basic methanol).

LL-D49194δ

Ultraviolet absorption spectra: as shown in FIG. XIV (methanol, acidic methanol, basic methanol).

LL-D49194ε

(1) Specific rotation: $[\alpha]_D^{26} = -123 \pm 4°(0.35\%$, CHCL$_3$);

(2) Ultraviolet absorption spectra: as shown in FIG. XV (methanol, acidic methanol, basic methanol);

(3) Infrared absorption spectrum: as shown in FIG. XVI (KBr disc);

(4) Proton magnetic resonance spectrum: as shown in FIG. XVII (300 MHz, CDCl$_3$);

(5) Carbon-13 magnetic resonance spectrum: as shown in FIG. XVIII (75.43 MHz, CDCl$_3$, ppm from TMS). Significant peaks as listed below:

16.5; 16.9; 17.6; 20.2; 20.9; 25.7; 25.9; 26.8; 35.7; 36.4; 36.6; 36.7; 53.0; 59.0; 62.3; 62.8; 62.9; 63.2; 63.8; 66.8; 67.9; 68.8; 69.2; 69.4; 70.5; 74.4; 84.0; 85.0; 94.7; 95.2; 97.6; 101.0; 105.9; 107.8; 108.2; 113.5; 114.1; 116.9; 126.7; 135.5; 142.5; 145.2; 152.3; 162.4; 170.3; 203.4.

LL-D49194ζ

Ultraviolet absorption spectra: as shown in FIG. XIX (methanol, acidic methanol, basic methanol).

LL-D49194η

(1) Specific rotation: $[\alpha]_D^{26} = \pm 65 + 3°(0.4\%$, ethanol);

(2) Ultraviolet absorption spectra: as shown in FIG. XX (methanol, acidic methanol, basic methanol);

(3) Infrared absorption spectrum: as shown in FIG. XXI (KBr disc);

(4) Proton magnetic resonance spectrum: as shown in FIG. XXII (300 MHz, CDCl$_3$);

(5) Carbon-13 magnetic resonance spectrum: as shown in FIG. XXIII (75.43 MHz, CDCl$_3$, ppm from TMS). Significant peaks as listed below:

16.7; 16.9; 20.3; 20.9; 25.7; 26.0; 34.6; 36.7; 47.8; 52.8; 58.6; 62.7; 62.9; 63.6; 67.5; 67.9; 68.8; 69.0; 69.1; 69.9; 71.3; 74.4; 94.3; 94.9; 98.0; 102.3; 104.3; 107.3; 114.8; 115.0; 116.7; 126.5; 135.5; 142.9; 148.8; 151.6; 163.2; 170.3; 202.8.

LL-D49194β$_3$ (1) Ultraviolet absorption spectra: as shown in FIG. XXIV (methanol, acidic methanol, basic methanol);

(2) (Proton magnetic resonance spectrum: as shown in FIG. XXV (300 MHz, CDCl$_3$);

(3) Carbon-13 magnetic resonance spectrum: as shown in FIG. XXVI (75.43 MHz, CDCl$_3$, ppm from TMS). Significant peaks as listed below:

16.7; 16.9; 20.3; 26.1; 34.6; 36.0; 36.7; 47.9; 52.8; 58.5; 62.7; 63.6; 67.6; 68.0; 69.0; 69.1; 69.9; 70.1; 71.3; 74.5; 94.3; 94.9; 98.2; 102.3; 104.4; 107.4; 114.9; 116.7; 126.7; 135.5; 142.9; 144.8; 151.6; 163.2; 202.9.

LL-D49194ω$_1$ (1) Ultraviolet absorption spectra: as shown in FIG. XXVII (methanol, acidic methanol, basic methanol);

(2) Proton magnetic resonance spectrum: as shown in FIG. XXVIII (300 MHz, CDCl$_3$);

(3) Carbon-13 magnetic resonance spectrum: as shown in FIG. XXIX (75.43 MHz, CDCl$_3$, ppm from TMS). Significant peaks as listed below:

16.5; 16.9; 17.6; 20.1; 26.2; 26.8; 35.7; 35.8; 36.0; 36.7; 53.0; 58.8; 62.2; 62.7; 63.6; 63.9; 67.2; 68.0; 69.3; 69.4; 70.0; 70.1; 70.6; 74.4; 84.0; 85.1; 94.8; 95.2; 98.0; 101.0; 106.0; 107.9; 108.3; 113.5; 114.1; 116.9; 127.1; 135.6; 142.4; 145.2; 152.4; 162.3; 203.5.

LL-D49194ω$_2$

Ultraviolet absorption spectra: as shown in FIG. XXX (methanol, acidic methanol, basic methanol).

LL-D49194ω$_3$ (1) Specific rotation: $[\alpha]_D^{26} = 0°(0.6\%$, ethanol);

(2) Ultraviolet absorption spectra: as shown in FIG. XXXI (methanol, acidic methanol, basic methanol);

(3) Infrared absorption spectrum: as shown in FIG. XXXII (KBr disc);

(4) Proton magnetic resonance spectrum: as shown in FIG. XXXIII (300 MHz, CDCl$_3$);

(5) Carbon-13 magnetic resonance spectrum: as shown in FIG. XXXIV (75.43 MHz, CDCl$_3$ ppm from TMS). Significant peaks as listed below:

16.7; 16.9; 20.2; 20.9; 25.7; 26.1; 34.7; 36.5; 36.7; 53.0; 58.8; 62.3; 62.8; 62.9; 63.6; 66.8; 67.9; 68.8; 69.4; 69.9; 70.5; 74.4; 85.1; 94.8; 95.3; 97.5; 106.0; 107.9; 108.3; 113.6; 114.0; 116.9; 126.7; 135.5; 142.5; 145.1; 152.3; 162.4; 170.3; 203.5.

The LL-D49194 components are most conveniently separated and identified by high-performance liquid chromatography (HPLC) and by thin-layer chromatography (TLC).

The preferred analytical separation of the LL-D49194 components by HPLC uses the following conditions:
Column: "Ultrasphere ODS," 4.6 mm×25 cm (Altex);
Solvent: Acetonitrile: 0.1M acetate buffer at pH 4.0 (35:65);
Flow rate: 1.5 ml/minute;
Detector: Dual wavelength UV at 280 nm and 405 nm;
Sensitivity: 0–0.05 A.U.F.S.

Table I gives the approximate retention times and volumes when 0.5 μg each of LL-D49194$\alpha_1$, LL-D49194$\beta_1$, LL-D49194$\beta_2$, LL-D49194$\beta_3$, LL-D49194$\delta$, LL-D49194$\zeta$, LL-D49194$\eta$, LL-D49194$\omega_1$, LL-D49194$\omega_2$ and LL-D49194$\omega_3$ and 1.0 μg of LL-D49194$\epsilon$ were coinjected.

TABLE I

| LL-D49194 Components | Retention Time (Minutes) | Retention Volume (ml) |
|---|---|---|
| $\alpha_1$ | 20.3 | 30.5 |
| $\beta_1$ | 9.1 | 13.7 |
| $\beta_2$ | 4.7 | 7.1 |
| $\beta_3$ | 4.0 | 8.6 |
| $\gamma$ | 15.3 | 23.0 |
| $\delta$ | 27.5 | 41.3 |
| $\epsilon$ | 42.2 | 63.3 |
| $\zeta$ | 13.7 | 20.6 |
| $\eta$ | 16.2 | 24.3 |
| $\omega_1$ | 2.8 | 4.2 |
| $\omega_2$ | 2.4 | 3.6 |
| $\omega_3$ | 7.3 | 11.0 |

The following analytical HPLC system can also be used for the separation of the LL-D49194 components:
Column: "Ultrasphere ODS," 4.6 mm×25 cm (Altex);
Solvent: Methanol: 0.1M acetate buffer at pH 4.0 (70:30);
Flow rate: 1.0 ml/minute;
Detector: Dual wavelength UV at 280 nm and 405 nm;
Sensitivity: 0–0.05 A.U.F.S.

Table II gives the approximate retention times and volumes when 0.5 μg each of components $\alpha_1$, $\beta_1$, $\beta_2$, $\beta_3$, $\gamma$, $\delta$, $\epsilon$, $\zeta$, $\eta$, $\omega_1$, $\omega_2$ and $\omega_3$ were injected separately or coinjected.

TABLE II

| LL-D49194 Components | Retention Time (Minutes) | Retention Volume (ml) |
|---|---|---|
| $\alpha_1$ | 7.0 | 7.0 |
| $\beta_1$ | 6.1 | 6.1 |
| $\beta_2$ | 4.6 | 4.6 |
| $\beta_3$ | 4.1 | 4.1 |
| $\gamma$ | 6.3 | 6.3 |
| $\delta$ | 10.6 | 10.6 |
| $\epsilon$ | 10.2 | 10.2 |
| $\zeta$ | 7.6 | 7.6 |
| $\eta$ | 6.4 | 6.4 |
| $\omega_1$ | 4.0 | 4.0 |
| $\omega_2$ | 3.7 | 3.7 |
| $\omega_3$ | 5.5 | 5.5 |

The LL-D49194 components are separated and identified by the following high performance TLC systems:
Adsorbant: LHP-K High Performance TLC plates with fluorescent indicator and preadsorbant area, Whatman;
Detection: Visualized by yellow-green flourescence under long wavelength UV lamp (366 nm), and bioautography using the biochemical induction assay;
Solvent System: I, dichloromethane:methanol (94:6); II, ethyl acetate saturated with 0.1M phosphate buffer at pH 7.0; III, ethyl acetate:glacial acetic acid (90:10).

Table III gives the approximate Rf values of the LL-D49194 components in these three systems:

TABLE III

| LL-D49194 Components | Rf Value Solvent System I | Rf Value Solvent System II | Rf Value Solvent System III |
|---|---|---|---|
| $\alpha_1$ | 0.36 | 0.30 | 0.51 |
| $\beta_1$ | 0.18 | 0.09 | 0.21 |
| $\beta_2$ | 0.20 | 0.13 | 0.31 |
| $\beta_3$ | 0.24 | 0.20 | 0.36 |
| $\gamma$ | 0.32 | 0.25 | 0.44 |
| $\delta$ | 0.27 | 0.16 | 0.29 |
| $\epsilon$ | 0.37 | 0.29 | 0.40 |
| $\zeta$ | 0.28 | 0.19 | 0.40 |
| $\eta$ | 0.35 | 0.43 | 0.56 |
| $\omega_1$ | 0.08 | 0.04 | 0.10 |
| $\omega_2$ | 0.09 | 0.06 | 0.14 |
| $\omega_3$ | 0.21 | 0.14 | 0.30 |

Methanolysis of LL-D49194$\beta_1$, using one percent gaseous hydrogen chloride in dry methanol at 0°, gives α and β anomers of methyl L-axenoside identified by their spectral data, optical rotations and melting points. Methanolysis of LL-D49194$\alpha_1$ and LL-D49194$\beta_1$ gives the same two methyl glycosides identified by TLC comparison to authentic samples derived from LL-D49194$\beta_1$.

DETAILED DESCRIPTION OF THE INVENTION

The new antibacterial and anti-tumor agents designated LL-D49194$\alpha_1$, LL-D49194$\beta_1$, LL-D49194$\beta_2$, LL-D49194$\beta_3$, LL-D49194$\gamma$, LL-D49194$\delta$, LL-D49194$\epsilon$, LL-D49194$\zeta$, LL-D49194$\eta$, LL-D49194$\omega_1$, LL-D49194$\omega_2$ and LL-D49194$\omega_3$ are formed during the cultivation under controlled conditions of a new strain of *Streptomyces vinaceus-drappus*. This new strain is maintained in the culture collection of the Medical Research Division, AMERICAN CYANAMID COMPANY, Pearl River, N.Y. as culture number LL-D49194. A viable culture of this new microorganism has been deposited with the Culture Collection Laboratory, Northern Utilization Research and Development Division, U.S. Department of Agriculture, Peoria, Ill., and has been added to its permanent collection. It is freely available to the public in this depository under its accession number NRRL 15735.

Culture LL-D49194 was isolated from a soil sample collected in La Encanada, Peru. The culture was taxonomically characterized and was identified as a strain of *Streptomyces vinaceus-drappus*, a know species of the red-spored streptomycetes.

Observations were made of the cultural, physiological and morphological features of the culture in accordance with the methods detailed by Shirling and Gottleib [Internat. J. Syst. Bacteriol., 16, 313–340 (1967)]. Media used in this study were selected from those recommended by Pridham, et al., [Antibiotics Ann. 1956/1957, 947–953 (1957)] for the taxonomic study of actinomycetes. Chemical composition of the cell walls of the culture was determined using the method of Lechevalier, et al. [Adv. Appl. Microbiol., 14, 47–72 (1971)]. Details are recorded in Table IV–VII, and a general description of the culture is given below. Underscored descriptive colors are taken from Kelly and Judd [Nat. Bur. Stand., Spec. Publ., 440 (1976)] and the accompanying Inter-Society Color Council, National Bureau of Standards Centroid Color Charts.

Micromorphology

Spores were formed in coiled chains (Spira) on aerial sporophores. The spores are ovoid (0.4–0.5 micron×0.9–1.0 micron) and the surface of the mature spores was smooth when observed by scanning electron microscopy.

Cell Wall Composition

Whole cell hydrolysates of this culture contain the L,L-isomer of diaminopimelic acid, placing it in the Type I cell wall group of Lechevalier, et al. (vide supra). This is typical of all Streptomyces species.

Amount of Growth

Good growth was observed on most media; moderate growth was observed on oatmeal agar.

Aerial Mycelium and Spore Color

Aerial mycelium was white; spore masses were gray to pinkish gray shades ranging from 264. light gray to 10. pinkish gray.

Soluble Pigments

Absent on many media; brownish shades where produced.

Reverse Color

Yellow to yellowish brown shades on all media.

Physiological Reactions

Nitrates reduced to nitrites in 7 days; no liquification of gelation in 14 days; no black pigment (melanin) produced on either peptone-yeast extract-iron agar or tyrosine agar; moderate peptonization of litmus milk in 14 days. Carbohydrate utilization as per the method of Pridham and Gottlieb [J. Bacteriol, 56, 107–114 (1948)]: good utilization of fructose, galactose, inositol, rhamnose and xylose; moderate utilization of arabinose, glucose, mannitol, salicin and sucrose; poor utilization of raffinose.

Culture LL-D49194 was compared with Streptomyces reference cultures which are known to produce antibiotics of this class, *Streptomyces bottropensis* NRRL 12051, and a reference culture of the red-spored streptomycete group closest to this train, *Streptomyces vinaceus-drappus* NRRL 2363. The following observations were made of 14-day growth on yeast extract-malt extract agar.

| Culture | Spore Mass Color | Soluble Pigments | Reverse Color |
| --- | --- | --- | --- |
| *S. bottropensis* NRRL 12051 | light grayish yellow-brown | reddish-brown | brownish black |
| *S. vinaceus-drappus* NRRL 2363 | light gray to pinkish gray | none | moderate orange-yellow |
| *S. vinaceus-drappus* LL-D49194 | light gray to pinkish gray | none | moderate orange-yellow |

Based on morphological and physiological culture LL-D49194 taxonomically resembles the reference strain of *Streptomyces vinaceus-drappus* and is designated as a strain of this species. There is no resemblance between culture LL-D49194 and *Streptomyces bottropensis* NNRL 12051, which produces different antibiotics of the same class.

TABLE IV

Cultural Characteristics of *Streptomyces vinaceus-drappus* LL-D49194

| Medium | Amount of Growth Incubation 14 Days at 28° C. | Aerial Mycelium and/or Spores | Soluble Pigment | Reverse Color |
| --- | --- | --- | --- | --- |
| Glycerol-Asparagine agar | Good to moderate | Slightly raised colonies with white aerial mycelia becoming 264. light gray to 10. pinkish gray in sporulated areas. | None | Light yellow |
| Hickey-Tresner agar | Good | Slightly raised colonies with white aerial mycelia becoming 264. light gray to 10. pinkish gray in sporulated areas; sporulation heavy. | None | Yellowish brown |
| Inorganic Salts-Starch agar | Good | Relatively flat growth with very heavy sporulation, 264. light gray. | Brownish | Deep yellow |
| Oatmeal agar | Moderate | Flat powdery growth with 264. light gray to 10. pinkish gray with 265. medium gray patches. | None | Yellowish white |
| Tomato Paste-Oatmeal agar | Good | Raised colonies with white aerial mycelia becoming 264. light gray to 10. pinkish gray where sporulated. | Brownish | |
| Yeast Extract-Malt Extract agar | Good | Raised, ridged colonies with white aerial mycelia becoming 10. pinkish gray in sporulated areas. | None | Moderate orange-yellow |

TABLE V

Micromorphology of *Streptomyces vinaceus-drappus* LL-D49194

| Medium | Aerial Mycelium and/or Sporiferous Structures | Spore Shape | Spore Size | Spore Surface |
| --- | --- | --- | --- | --- |
| Yeast Extract-Malt Extract agar | Spore chains arise as coiled chains from aerial sporophores | ovoid | 0.4–0.5 micron × 0.9–1.0 micron | smooth |

TABLE V-continued

| Medium | Micromorphology of *Streptomyces vinaceus-drappus* LL-D49194 | | | |
|---|---|---|---|---|
| | Aerial Mycelium and/or Sporiferous Structures | Spore Shape | Spore Size | Spore Surface |
| | (Spira) | | | |

TABLE VI

Physiological reactions of *Streptomyces vinaceus-drappus* LL-D49194

| Medium | Incubation Period(Days) | Amount of Growth | Physiological Reaction |
|---|---|---|---|
| Peptone-Iron agar | 7 | Good | No blackening |
| | 14 | Good | No blackening |
| Tyrosine agar | 7 | Good | No blackening |
| | 14 | Good | No blackening |
| Litmus milk | 7 | Good | Slight proteolysis |
| | 14 | Good | Moderate proteolysis |
| Nutrient gelatin | 7 | Good | No proteolysis |
| | 14 | Good | No proteolysis |
| Nitrate broth | 7 | Good | Reduction |

TABLE VII

Carbon Source Utilization of *Streptomyces vinaceus-drappus* LL-D49194 (Incubation 14 days, 28° C.)

| Carbon Source | Utilization* |
|---|---|
| l-Arabinose | 2 |
| Fructose | 3 |
| d-Galactose | 3 |
| d-Glucose | 2 |
| i-Inositol | 3 |
| d-Mannitol | 2 |
| d-Raffinose | 1 |
| l-Rhamnose | 3 |
| Salicin | 2 |
| Sucrose | 2 |
| Xylose | 3 |
| Negative control | 0 |

*3 = Good utilization
2 = Fair utilization
1 = Poor utilization
0 = No utilization It is to be understood that for the production of these new antibacterial and anti-tumor agents the present invention is not limited to this particular organism or to organisms fully answering the above growth and microscopic characteristics which are given for illustrative purposes only. In fact, it is desired and intended to include the use of mutants produced from this organism by various means such as exposure to X-radiation, ultraviolet radiation, N'-methyl-N'-nitro-N-nitrosoguanidine, actiophages and the like.

The in vitro antibacterial activity of LL-D49194$\alpha_1$, LL-D49194$\beta_1$, and LL-D49194$\beta_2$ was determined against a spectrum of gram-positive and gram-negative bacteria by a standard agar dilution method. Mueller-Hinton agar containing two-fold decreasing concentrations of the antibiotics were poured into petri plates. The agar surfaces were inoculated with 1 to $5 \times 10^4$ colony forming units of bacteria by means of the Steers replicating device. The lowest concentration of antibiotic that inhibited growth of a bacterial strain after 18 hours of incubation at 35° C. was recorded as the minimal inhibitory concentration (MIC) for the strain. The results are summarized in Table VIII.

TABLE VIII

In vitrol Antibacterial Activity of LL-D49194$\alpha$ and LL-D49194$\beta$

| Organism | Minimal Inhibitory Concentration (mcg/ml) | | |
|---|---|---|---|
| | LL-D49194$\alpha_1$ | LL-D49194$\beta_1$ | LL-D49194$\beta_2$ |
| Gram-negative bacteria | | | |
| *Escherichia coli* Stfd-79-20 | >128 | >128 | >128 |
| *Escherichia coli* #311 | >128 | >128 | >128 |
| *Klebsiella pneumoniae* AD | >128 | >128 | >128 |
| *Acinetobacter calcoaceticus* K-77-1 | >128 | >128 | >128 |
| *Pseudomonas aeruginosa* SSC-78-13 | >128 | >128 | >128 |
| *Pseudomonas aeruginosa* 12-4-4 | >128 | >128 | >128 |
| *Pseudomonas aeruginosa* ATCC 27853 | >128 | >128 | >128 |
| Gram-positive bacteria | | | |
| *Staphylococcus aureus* SSC-79-18 | 1 | 512 | 2 |
| *Staphylococcus aureus* Smith | 0.5 | 512 | 1 |
| *Staphylococcus aureus* ATCC 25923 | 2 | 512 | 8 |
| *Micrococcus lutea* PCI 1001 | 0.5 | >512 | 1 |
| *Enterococcus sp.* OSU-75-1 | 2 | >512 | 8 |
| *Enterococcus sp.* SSC-81-1 | 2 | >512 | 4 |
| *Bacillus subtilis* ATCC 6633 | 0.5 | >512 | 0.5 |

Each of the components of LL-D49194 were also found to be active in a modification of the Biochemical Induction Assay [Elespuru, R. and Yarmolinsky, M., Environmental Mutagenesis, 1, 65–78 (1979)], a test which specifically measures the ability of an agent to directly or indirectly initiate DNA damage.

In this assay LL-D49194$\alpha_1$ was active at a minimal concentration of 0.1 mcg/ml, LL-D49194$\beta_1$ was active at 100 mcg/ml and LL-D49194$\beta_2$ was active at 2 mcg/ml.

Certain in vivo testing systems and protocols have been developed by the National Cancer Institute for testing compounds to determine their suitability as antineoplastic agents. These have been reported in "Cancer Chemotherapy Reports", Part III, Vol. 3, No. 2 (1972), Deran, et al. These protocols have established standardized screening tests which are generally followed in the field of testing for antitumor agents. Of these systems, lymphocytic leukemia P388, melanotic melanoma B16, L1210 leukemia and colon 26 adenocarcinoma are particularly significant to the present invention. These neoplasms are found in mice. Generally, good antitumor activity, shown in these protocols by a percentage increase of mean survival times of the treated animals (T) over the control animals (C), is predictive of similar results in human leukemias.

The novel compounds of the present invention possess the property of inhibiting the growth of transplanted mouse tumors as established by the following tests.

Lymphocytic Leukemia P388 Test

The animals used were $BDF_1$ mice, all of one sex, weighing a minimum of 17 g and all within a 3 g weight range. There were 5 to 6 mice per test group. The tumor transplant was by intraperitoneal injection of 0.5 ml of dilute ascitic fluid containing $10^6$ cells of lymphocytic leukemia P388. The test compounds are administered intraperitoneally at a volume of 0.5 ml in 0.2% klucel in normal saline on days 1, 5 and 9 (relative to tumor inoculation) at the indicated doses. The mice were weighed and the survivors recorded on a regular basis for 30 days. The median survival time and the ratio of survival time for treated (T)/control (C) animals were calculated. The positive control compound for LL-D49194$\alpha_1$ and $\beta_1$ was 1,4-dihydroxy-5,8-bis[[2-(2-hydroxyethylamino)ethyl]amino]-anthraquinone, dihydrochloride (U.S. Pat. No. 4,197,249) and for LL-D49194$\beta_2$ was Cisplatin given as an intraperitoneal injection in 0.5 ml of 0.2% klucel on days 1, 5 and 9 at the indicated doses. The results appear in Table IX.

TABLE IX

Lymphocytic Leukemia P388 Test

| Compound | Dose (mg/kg) | Median survival (Days) | T/C × 100 (%) |
|---|---|---|---|
| LL-D49194$\alpha_1$ | 0.2 | 18.5 | 154 |
|  | 0.4 | 14.5 | 121 |
| Control | — | 12.0 | — |
| Positive Control | 0.4 | 20.5 | 171 |
| LL-D49194$\alpha_1$ | 0.05 | 21.0 | 196 |
|  | 0.1 | 12.0 | 112 |
| Control | — | 10.7 | — |
| Positive Control | 0.4 | 21.0 | 196 |
| LL-D49194$\beta_1$ | 400 | 20.5 | 171 |
|  | 200 | 16.0 | 133 |
|  | 100 | 15.5 | 129 |
|  | 50 | 15.0 | 125 |
| Control | — | 12.0 | — |
| Positive Control | 0.4 | 20.5 | 171 |
| LL-D49194$\beta_1$ | 200 | 19.0 | 143 |
|  | 100 | 19.5 | 147 |
|  | 50 | 18.0 | 135 |
|  | 25 | 16.0 | 120 |
| Control | — | 13.3 | — |
| Positive Control | 0.4 | >30.0 | >226 |
| LL-D49194$\beta_2$ | 2 | 16.5 | 154 |
|  | 1 | 15.5 | 145 |
|  | 0.5 | 13 | 121 |
|  | 0.25 | 12 | 112 |
| Control | — | 10.7 | — |
| Cisplatin | 3 | 14 | 131 |
|  | 1.5 | 21 | 196 |
|  | 0.8 | 19.5 | 182 |
|  | 0.4 | 15 | 140 |

Melanotic Melanoma B16

The animals used were $BDF_1$ mice, all of the same sex, weighing a minimum of 17 g and all within a 3 g weight range. There are normally 6 animals per test group. A 1 g portion of melanotic melanoma $B_{16}$ tumor was homogenized in 10 ml of cold balanced salt solution and a 0.5 ml aliquot of the homogenate was implanted intraperitoneally into each of the test mice. The test compounds were administered intraperitoneally on days 1 through 9 (relative to tumor inoculation) at various doses. The mice were weighed and survivors recorded on a regular basis for 60 days. The median survival time and the ratio of survival time for treated (T)/control (C) animals were calculated. The positive control compounds used were 1,4-dihydroxy-5,8-bis[[2-(2-hydroxyethylamino)-ethyl]amino]anthraquinone, dihydrochloride (U.S. Pat. No. 4,197,249), bis (2-imidazolin-2-yl-hydrazone)-9,10-anthracenedicarboxaldehyde, dihydrochloride (U.S. Pat. No. 4,258,181) and Cisplatin. The results of this test appear in Table X.

TABLE X

Melanotic Melanoma $B_{16}$ Test

| Compound | Dose (mg/kg) | Median Survival (Days) | T/C × 100 (%) |
|---|---|---|---|
| LL-D49194$\alpha_1$ | 0.125 | 31.5 | 150 |
| Control | — | 21.0 | — |
| bis(2-(imidazolin-2-ylhydrazone)-9,10-anthracenedicarboxaldehyde, dihydrochloride | 0.8 | 48 | 176 |
| LL-D49194$\beta_1$ | 200 | 50.0 | 229 |
|  | 100 | 34.5 | 158 |
|  | 50 | 36.5 | 167 |
| Control | — | 21.8 | — |
| 1,4-dihydroxy-5,8-bis[[2-(2-hydroxyethylamino)ethyl]-amino]anthraquinone,dihydrochloride | 0.4 | >60 | >275 |
| LL-D49194$\beta_2$ | 0.5 | 36 | 195 |
|  | 0.25 | 35.5 | 192 |
|  | 0.125 | 35 | 189 |
|  | 0.06 | 27 | 146 |
|  | 0.03 | 20.5 | 111 |
| Control | — | 18.5 | — |
| Cisplatin | 0.5 | 27 | 146 |
|  | 0.25 | 27.5 | 149 |
|  | 0.125 | 23.5 | 127 |

Lymphocytic Leukemia L1210 Test

The animals used were $BDF_1$ or $CD_2F_1$ mice, all of one sex, weighing a minimum of 17 g and all within a 3 g weight range. There were 6 mice in each test group and 18 in control groups. The tumor transplant was by intraperitoneal injection of 0.5 ml of lymphocytic leukemia L1210 at a concentration of $10^5$ cells per mouse. The test compounds were administered on days 1, 5 and 9 (relative to tumor inoculation) at various doses. The mice were weighed and survivors recorded on a regular basis for 30 days. The median survival time and the ratio of survival time for treated (T)/control (C) animals were calculated. The positive control compound was 5-fluorouracil given intraperitoneally at the indicated dose. The results appear in Table XI.

TABLE XI

Lymphocytic Leukemia L1210 Test

| Compound | Dose (mg/kg) | Median Survival (Days) | T/C × 100 (%) |
|---|---|---|---|
| LL-D49194$\beta_1$ | 200 | 12.0 | 126 |
| 5-Fluorouracil | 50 | 14.5 | 153 |
|  | 25 | 11.5 | 121 |
| Control | 0 | 9.5 | — |

Colon 26 Adenocarcinoma Test

The animals used were Balb/C mice all of one sex, weighing a minimum of 17 g and all within a 3 g weight range. There were 5 or 6 mice per test group with three groups of 5 or 6 animals used as untreated controls for each test. The tumor implant was by intraperitoneal (or subcutaneous) injection of 0.5 ml of a 2% Colon 26 tumor brei in Eagle's MEM medium containing antibiotics. The LL-D49194 preparations were administered intraperitoneally on days 1, 5 and 9 (relative to tumor implant doses). The mice were weighed and deaths recorded on a regular basis for 30 days. The median survival times for treated (T)/control (C) animals were calculated. The positive control compounds were 5-fluorouracil and Cisplatin. The results appear in Table XII.

TABLE XII

Colon 26 Adenocarcinoma Test

| Compound | Dose (mg/kg) | Median Survival (Days) | T/C × 100 (%) |
|---|---|---|---|
| LL-D49194$\beta_1$ | 50 | 28, 42 | 133, 150 |
| Control | — | 21 | — |
| 5-Fluorouracil | 12 | 30 | 171 |
| LL-D49194$\beta_2$ | 2 | 21.5 | 110 |
|  | 1 | 21.5 | 110 |
|  | 0.5 | 23.5 | 121 |
| Control | — | 19.5 | — |
| Cisplatin | 1 | 31.4 | 161 |
|  | 0.5 | 29 | 150 |

General Fermentation Conditions

Cultivation of *Streptomyces vinaceus-drappus* NRRL 15735 may be carried out in a wide variety of liquid culture media. Media which are useful for the production of these novel antibacterial and anti-tumor agents include an assimilable source of carbon, such as starch, sugar, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, choride, etc. Trace elements such as born, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone may be added as needed.

General Procedure for the Isolation and Separation of LL-D49194$\alpha_1, \beta_1, \beta_2, \gamma, \delta, \epsilon, \zeta$ and $\eta$ The LL-D49194 antibiotics are recovered from the fermentation broth by adsorption of the fermentation filtrate on a column of macroreticular resin such as Amberlite ® XAD-2 (Rohm and Haas Co.) and elution from the column by aqueous acetone or aqueous alcohol mixtures. The active preparations are further purified by partition between dichloromethane and water or ethyl acetate and water. The LL-D49194 antibiotics, contained in the organic phase, are concentrated and further purified by precipitated from lower hydrocarbons or diethyl ether, or by flash chromatography on silica gel. Final separation of the individual components is achieved by repeated silica gel chromatography using dichloromethane containing varied amounts of methanol.

It is also possible to isolate LL-D49194 antibiotics from the mycelium by extracting the cells with aqueous acetone or aqueous methanol, concentrating the extract and extracting the aqueous concentrate with dichloromethane or ethyl acetate. The organic phase containing the antibiotic is then concentrated and chromatographed on silica gel as described above.

The invention will be described in greater detail in conjunction with the following non-limiting specific examples.

EXAMPLE 1

Inoculum Preparation

A typical medium used to grow the primary inoculum was prepared according to the following formula:

| Beef extract | 0.3% |
|---|---|
| Tryptone | 0.5% |
| Dextrose | 1.0% |
| Yeast extract | 0.5% |
| Water qs to | 100% |

This medium was adjusted to pH 7.0 and then sterilized. A 100 ml portion of this sterile medium, in a flask, was inoculated with mycelial scrapings from an agar slant of the culture *Streptomyces vinaceus-drappus* NRRL 15735. The medium was then placed on a rotary shaker and agitated vigorously for 48–72 hours at 180–200 rpm and 28° C. This incubated medium was used to inoculate fermentation medium or second stage inoculum flasks when a larger quantity of the inoculum was needed. Fifty ml. portions of sterile primary inoculum in 250 ml flasks were inoculated with 1.5 ml of frozen seed prepared from the primary inoculum. This medium was incubated at 28° C. and 180–200 rpm for two days. This inoculum was then used to inoculate 500 ml flasks each containing 100 ml of the same sterile medium. The flasks were incubated at 28° C. and 180–200 rpm for 24–48 hours and they provide the seed inoculum.

EXAMPLE 2

Flask Fermentation

Inoculum prepared as described in Example 1 was used to inoculate flasks containing sterile fermentation medium. A typical fermentation medium has the following composition:

| Bacto peptone | 0.5% |
|---|---|
| Glucose | 1.0% |
| Molasses | 2.0% |
| Calcium carbonate | 0.1% |
| Water qs to | 100% |

The medium was adjusted to pH 7.0 sterilized and distributed at the rate of 100 ml per 500 ml flask. Each flask was inoculated with 5 ml of the final seed inoculum from Example 1 and incubated at 28° C. on a rotary shaker at 180–200 rpm for four to six days at which time the fermentation broths were combined and harvested. Samples of the fermentations were monitored for production of the LL-D49194 antibiotics by antibacterial activity, biochemical induction assay, TLC and HPLC analyses.

EXAMPLE 3

Tank Fermentation

A primary inoculum medium was prepared according to the following formula:

| Tryptone | 0.5% |
|---|---|
| Yeast extract | 0.5% |
| Beef extract | 0.3% |

| | |
|---|---|
| Dextrose | 1.0% |
| Water qs to | 100% |

The medium was sterilized and 100 ml portions in individual flasks were inoculated with scrapings from an agar slant of Streptomyces vinaceus-drappus NRRL 15735. These flasks were placed on a rotary shaker and agitated vigorously for 72 hours at 28° C.

A 200 ml portion of this primary inoculum was used to inoculate 12 liters of the same sterile medium which was aerated and grown at 28° C. for 48 hours, providing secondary inoculum.

A 12 liter portion of this secondary inoculum was used to inoculate 270 liters of the same sterile medium in a tank. This tertiary inoculum was grown at 32° C. for 48 hours with aeration of 200 liters of sterile air per minute and agitation at 350 rpm.

A fermentation medium was prepared according to the following formula:

| | |
|---|---|
| Molasses | 2.0% |
| Dextrose | 1.0% |
| Bacto peptone | 0.5% |
| Calcium carbonate | 0.1% |
| Water qs to | 100% |

A 2600 liter portion of this medium was sterilized and then inoculated with 300 liters of the above tertiary inoculum. Aeration was supplied at the rate of 1760 liters of sterile air per minute and agitation was supplied by an impeller driven at 145 rpm. The temperature was maintained at 28° C. and the fermentation was terminated after 97 hours at which time the mash was harvested. The fermentation was monitored for production of LL-D49194 antibiotics by antibacterial activity, biochemical induction assays, TLC and HPCL analyses.

EXAMPLE 4

Isolation of LL-D49194$\alpha_1$ and LL-D49194$\beta_1$

A 6.0 liter portion of whole fermentation broth, from a fermentation conducted as described in Example 2, was passed through filter paper. The filtrate was loaded onto a 2.5×50 cm column, containing 250 ml of Amerlite ® XAD-2 resin (Rohm and Haas Co.), at the rate of 16 ml/minute. The column was eluted at a rate of 1.2 ml/minute, collecting 15 ml fractions, first with acetone:water (20:80) for 4 hours, then with a linear gradient of acetone:water (20:80 to 80:20) for 4 hours and finally with acetone:water (80:20) for 6 hours. Fractions 39-56, containing the desired bioactivity, were pooled, concentrated and freeze-dried, giving 1.0 g of a brown gum. This material was partitioned between 200 ml each of dichloromethane and water and the aqueous phase was reextracted once with 200 ml of dichloromethane. The organic phases were combined, dried over anhydrous sodium sulfate and concentrated to dryness. This solid was then dissolved in a small amount of dichloromethane and chromatographed on a 1.5×9.0 cm column of silica gel (Kiesel Gel 60, 40-63μ, EM Products for Chromatography) packed and equilibrated with dichloromethane:methanol (95.5), at a flow rate of 1.5 ml/minute, collecting 15 ml fractions. Ater 24 fractions were collected, the eluent was changed to dichloromethane:methanol (90:10), and the elution was continued until a total of 63 fractions were collected. Each fraction was analyzed by bioassay, as well as TLC.

Fractions 13-32, containing pure LL-D49194$\alpha_1$, were pooled and concentrated to a small volume. Hexane was added to the concentrate and the yellow precipitate was collected, giving 46 mg of LL-D49194$\alpha_1$.

Fractions 37-56, containing pure LL-D49194$\beta_1$, were pooled, concentrated and precipitated with hexane, giving 66 mg of LL-D49194$\alpha_1$.

EXAMPLE 5

Isolation of LL-D49194$\alpha_1$, LL-D49194$\beta_1$, LL-D49194$\beta_2$, LL-D49194$\gamma$, LL-D49194$\delta$, LL-D49194$\epsilon$, LL-D49194$\zeta$, and LL-D49194$\eta$ Twenty-nine hundred liters of whole harvest mash from a fermentation conducted as described in Example 3 was filtered through a plate and frame press using 116 kg of Celite ® 512 as filter aid. The filtrate was passed through a 46 cm×140 cm Amberlite ® XAD-2 resin column. The column was washed with 400 liters of 20% aqueous acetone and then eluted with 1000 liters of 80% aqueous acetone. Forty 25 liter fractions were collected. Active fractions numbers 5 through 10 were pooled and concentrated to give 13 liters of aqueous mixture. The aqueous mixture was extracted three times with 20 liter portions of ethyl acetate. The ethyl acetate extracts were combined and concentrated to a residue. This residue was dissolved in 500 ml of dichloromethane:methanol (90:10). Each 100 ml portion of the above was chromatographed on a separate 2.5×110 cm silica gel column (Kiesel Gel 60, 40-63μ, EM Products for Chromatography) packed and equilibrated with dichloromethane:methanol (90:10), at a flow rate of 1.5 ml/minute, collecting 15 ml fractions. Each fraction was analyzed by bioassay and TL and the fractions containing LL-D49194$\alpha_1$ and LL-D49194$\beta_1$, as well as the minor components chromatographing together, were pooled and concentrated to yield a total of 60 ml of LL-D-49194 complex concentrate from the five silica gel columns. Fractions chromatographing after $\beta_1$, containing minor components $\omega_1$ and $\omega_2$, were also pooled and concentrated. Approximately 20 ml of the concentrate containing LL-D49194$\alpha_1$ and $\beta_1$ was chromatographed on a 2.5×110 cm column of the same type silica gel, packed and equilibrated and dichloromethane:methanol (95.5), at a flow rate of 1.5 ml/minute, collecting 15 ml fractions. Each fraction was analyzed as described above and those containing primarily LL-D49194$\alpha_1$ were pooled separately from those containing LL-D49194$\beta_1$.

The LL-D49194$\beta_1$ pool was concentrated and precipitated as described in Example 4, giving 1.2 g of LL-D49194$\beta_1$.

The LL-D49194$\alpha_1$ pool was concentrated and rechromatographed a 1.5×100 cm column containing the same type silica gel, packed and equilibrated with dichloromethane. The column was eluted with dichloromethane:methanol (98:2) at a flow rate of 1 ml/minute, collecting 10 ml fractions. The fractions were analyzed as described above and those fractions containing each of the individual $\alpha_1$, $\beta_2$, $\gamma$, $\delta$, $\epsilon$, $\zeta$ and $\eta$ components were pooled separately. The pooled fractions containing LL-D49194$\alpha_1$ were concentrated and precipitated as described in Example 4, giving 256 mg of LL-D49194$\alpha_1$.

Each of the pooled fractions containing minor components $\gamma$, $\delta$, $\epsilon$, $\zeta$, and $\eta$ were concentrated and further purified by revere phase preparative TL [Whatman PLKC$_{18}$F 1000 μm precoated TLC plates, acetonitrile:0.1M acetate buffer at pH 4.0 (45:55) elution]. In each case, the major blue-green fluorescent band, visualized under long wavelength UV lamp (366 nm) was removed from the plate and the antitumor agent was recovered by washing the absorbant with acetonitrile. The acetonitrile solutions were concentrated to dryness, redissolved in dichloromethane, filtered through anhydrous magnesium sulfate and concentrated to dryness. Each concentrate was then redissolved in a trace amount of dichloromethane and precipitated by the addition of hexane. After carefully removing the supernatants each precipitate was air dried, giving 0.5 to 1.0 mg each of LL-D49194γ, LL-D49194δ, LL-D49194ε, LL-D49194ζ and LL-D49194Lη.

The pooled fractions containing minor component LL-D49194β$_2$ were rechromatographed on a 1.5×100 cm column containing the same type silica gel, packed equilibrated and eluted with dichloromethane:methanol (96:4). The fractions were collected and analyzed as described above and those containing LL-D49194β$_2$ were pooled, concentrated and precipitated as described in Example 4, giving 38 mg of LL-D49194β$_2$.

Another 20 ml of the LL-D49194 complex concentrate (p. 43, line 9) from the first silica gel column chromatography was chromatographed on a 2.5×110 cm column of the same type silica gel packed and equilibrated with dichloromethane:methanol (98:2). The column was eluted with the same solvent system at a flow rate of 1.5 ml/minute overnight. The eluting solvent was changed to dichloromethane:methanol (95:5) and elution continued for one day. Finally, the column was eluted with dichloromethane methanol (90:10). The fractions collected (every 10 minutes) through out the elution were analyzed as described before and those containing minor components β$_3$ and ω$_3$ chromatographing between major components α$_1$ and β$_1$, were pooled and concentrated. Pure β$_3$ and ω$_3$ (1.0 to 2.0 mg each) were obtained by repeated reverse phase preparative TLC as described before and preparative TLC on silica gel (silica gel GF precoated plates, Analtech) developing with dichloromethane:methanol (96:4) or ethyl acetate saturated with 0.1M phosphate buffer at pH 7.0.

Pure LL-D49194ω$_1$ and ω$_2$ were isolated from the concentrate containing ω$_1$ and ω$_2$ from the first silica gel column chromatography (p. 43, line 9) by repeated reverse phase preparative TLC [Whatman PLKC$_{18}$F precoated TLC plates, acetonitrile:0.1M acetate buffer at pH 4.0 (35:65) or methanol:0.1M acetate buffer at pH 4.0 (50:50) elution] and preparative TLC on silica gel [Silica gel GF precoated plates, Analtech, 2% methanol in ethyl acetate saturated with 0.1M phosphate buffer at pH 7.0 elution].

EXAMPLE

Isolation of methyl α-β-L-axenosides from the methanolysate of LL-D49194β$_1$

A 300 mg portion of LL-D49194β$_1$ was dissolved in 100 ml of methanol. The solution was stirred and chilled to 0° C. A 100 ml solution of 1% hydrogen chloride in methanol was added dropwise and stirring continued at 0° C. for 20 minutes. The mixture was then neutralized by the addition of Amberlite ® IR45 (OH—form) ion exchange resin. The mixture was filtered and the filtrate concentrated in vacuo to dryness. The residue was partitioned between 100 ml of dichloromethane and 100 ml of water. The aqueous phase, containing the methyl glycosides was lyophilized giving a brown residue. The portion of this residue which was soluble in dicholoromethane was further purified by preparative TLC using a precoated Whatman preparative silica gel plate (PLK5F, 20×20 cm, 1000μ layer) developing with 5% methanol in dichloromethane. The two anomeric glycosides thus separated were further purified by recrystallization from mixtures of dichloromethane and hexane to give the following:

(a) 14 mg of methyl 2,6-dideoxy-3-c-methyl-α-L-xylo-hexopyranoside (methyl α-L-axenoside):mp 102°–103° C.; $[\alpha]_D^{26}$ −129±9° (c 0.15, chloroform); $^1$HNMR (CDCl$_3$, 300 MHz) δ1.247 (S, 3), 1259 (d, 3, J=7.0 Hz), .1664 (bd, 1, J=13.5 Hz), 1.812 (d, 1, J=8.2 Hz), 1.922 (dd, 1, J=14.6 Hz, 3.9 Hz), 3.135 (bd, 1, J=8.1 Hz), 3.381 (S, 3), 4.016 (bs, 1), 4.299 (bq, 1, 6.6 Hz), 4.799 (bd, 1, J=3.8 Hz); $^{13}$CNMR (CDCl$_3$, 300 MHz) δ16.7, 26.1, 35.5, 55.1, 62.5, 70.2, 74.6, 99.1; mass spectrum, m/z (relative intensity) 177 (2), 145(100), 127(19);

(b) 34 mg of methyl 2,6-dideoxy-3-c-methyl-β-L-xylo-hexopyranoside (methylβ-L-axenoside); mp 122°–123° C.; $[\alpha]_D^{26}$+24±6° C. (c 0.125, ethanol); $^1$HNMR (CDCl$_3$, 300 MHz) δ1.276 (d, 3, J=6.6 Hz), 1.341 (s, 3), 1.531 (bs, 1), 1.598 (dd, 1, J=14.0 Hz, 9.1 Hz), 1.677 (dd, 1, J=14.1 Hz, 2.9 Hz), 2.147 (d, 1, J=10.1 Hz), 2.974 (bd, 1, 10.1 Hz), 3.491 (s, 3), 4.128 (bq, 1, J=6.5 Hz), 4.615 (dd, 1, J=9.1 Hz, 3.1 Hz); $^{13}$CNMR (CDCl$_3$, 300 MHz) δ16.6, 27.8, 39.1, 56.4, 68.9, 72.5, 74.4, 100.4; mass spectrum, m/z (relative intensity) 177(2.5), 145(100), 172(27).

The physical constants of methyl α-L-axenoside have been reported by Garegg and Norber, Acta Chemical Scandinavia, B29, 507–512 (1975)

We claim:

1. Antitumor agent LL-D49194α$_1$, a composition which:

(a) is effective as an antitumor agent;
(b) is effective as an antibacterial agent;
(c) has a molecular weight of 992;
(d) has a molecular formula: C$_{48}$H$_{64}$O$_{22}$;
(e) has a melting point of 173°–176° C. (with decomposition);
(f) has a specific rotation: $[\alpha]_D^{26}$ =0°(0.57%, ethanol);
(g) has ultraviolet absorption spectra as shown in FIG. I of the drawings;
(h) has an infrared absorption spectrum as shown in FIG. II of the drawings;
(i) has a proton magnetic resonance spectrum as shown in FIG. III of the drawings;
(j) has a carbon-13 magnetic resonance spectrum as shown in FIG. IV of the drawings with significant peaks at
16.5; 16.9; 17.6; 20.4; 20.9; 25.7; 26.2; 26.7; 35.6; 36.7; 47.8; 52.8; 58.8; 62.7; 62.9; 63.9; 67.4; 67.9; 68.8; 69.0; 69.1; 69.2; 70.1; 71.3; 74.3; 74.4; 83.9; 94.2; 94.8; 97.9; 101.0; 102.3; 104.3; 107.3; 114.8; 114.9; 116.7; 126.5; 135.4; 142.9; 144.8; 151.5; 163.2; 170.3; 202.8; and (k) releases methyl α-L-axenoside and methyl β-L-axemoside upon treatment with dilute methanolic hydrochloric acid.

2. Antitumor agent LL-D49194β$_1$ a composition which:

(a) is effective as an antitumor agent;
(b) is effective as an antibacterial agent;

(c) has a molecular weight of 1010;
(d) has a molecular formula: $C_{48}H_{66}O_{23}$;
(e) has a melting point 163°–167° C. (with decomposition);
(f) has specific rotation;
   $[\alpha]_D^{26} = -51 \pm 10°(0.137\%, \text{ethanol})$
   $[\alpha]_D^{26} = -119 \pm 10°(0.135\%, \text{chloroform})$;
(g) has ultraviolet absortpion spectra as shown in FIG. V of the drawings;
(h) has an infrared absorption spectrum as shown in FIG. VI of the drawings;
(i) has a proton magnetic resonance spectrum as shown in FIG. VII of the drawings:
(j) has a carbon-13 magnetic resonance spectrum as shown in FIG. VIII of the drawings with significant peaks at
   16.5; 16.9; 17.6; 20.1; 20.8; 25.8; 26.3; 26.8; 35.7; 35.8; 36.7; 36.8; 53.0; 58.7; 62.3; 62.7; 62.9; 63.9; 67.1; 67.9; 68.8; 69.3; 69.4; 70.1; 70.7; 74.3; 74.5; 84.0; 85.1; 94.9; 95.2; 97.7; 101.0; 106.0; 107.9; 108.3; 113.6; 114.1; 116.8; 126.8; 135.5; 142.4; 145.1; 152.3; 162.4; 170.3; 203.6; and
(k) releases methyl α-L-axenoside and methyl β-L-axenoside upon treatment with dilute methanolic hydrochloric acid.

3. Antitumor agent LL-D49194β₂, a composition which:
(a) is effective as an antitumor agent;
(b) is effective as an antibacterial agent;
(c) has a specific rotation;
   $[\alpha]_D^{26} = +40 \pm 6°$ (0.15%, ethanol);
(d) has ultraviolet absorption spectra as shown in FIG. IX of the drawings;
(e) has an infrared absorption spectrum as shown in FIG. X of the drawings;
(f) has a proton magnetic resonance spectrum as shown in FIG. XI of the drawings;
(g) has a carbon-13 magnetic resonance spectrum as shown in FIG. XII of the drawingss with significant peaks at
   16.5; 16.9; 17.6; 20.3; 26.1; 26.2; 26.7; 35.6; 35.9; 36.6; 47.9; 52.8; 58.7; 62.7; 63.6; 63.9; 67.6; 68.0; 69.0; 69.1; 69.3; 70.1; 70.2; 71.2; 74.2; 74.4; 83.9; 94.2; 94.8; 98.1; 101.0; 102.3; 104.2; 107.4; 114.8; 114.9; 116.6; 126.6; 135.5; 142.9; 144.7; 151.5; 163.2; 202.9; and
(h) releases methyl α-L-axenoside and methyl β-L-axenoside upon treatment with dilute methanolic hydrochloric acid.

4. Antitumor agent LL-D49194β₃, a composition which:
(a) is effective as an antitumor agent;
(b) is effective as an antibacterial agent;
(c) has ultraviolet absorption spectra as shown in FIG. XXIV of the drawings;
(d) has a proton magnetic resonance spectrum as shown in FIG. XXV of the drawings; and
(e9 has a carbon-13 magnetic resonance spectrum as shown in FIG. XXVI of the drawings with significant peaks at
   16.7; 16.9; 20.3; 26.1; 34.6; 36.0; 36.7; 47.9; 52.8; 58.5; 62.7; 63.6; 67.6; 68.0; 69.0; 69.1; 69.9; 70.1; 71.3; 74.5; 94.3; 94.9; 98.2; 102.3; 104.4; 107.4; 114.9; 116.7; 126.7; 135.5; 142.9; 144.8; 151.6; 163.2; 202.9.

5. Antitumor agent LL-D49194γ, a composition which:
(a) is effective as an antitumor agnent;
(b) is effective as an antibacterial agent; and
(c) has ultraviolet absorption spectra as shown in FIG. XIII of the drawings.

6. Antitumor agent LL-D49194δ, a composition which:
(a) is effective as an antitumor agent;
(b) is effective as an antibacterial agent; and
(c) has ultraviolet absorption spectra as shown in FIG. XIV of the drawings.

7. Antitumor agent LL-D49194ε, a composition which:
(a) is effective as an antitumor agent;
(b) is effective as an antibacterial agent;
(c) has a specific rotation:
   $[\alpha]_D^{26} = -123 \pm 4°$ (0.35%, CHCl₃);
(d) has ultraviolet absorption spectra as shown in FIG. XV of the drawings;
(e) has an infrared absorption spectrum as shown in FIG. XVI of the drawings;
(f) has a proton magnetic resonance spectrum as shown in FIG. XVII of the drawings; and
(g) has a carbon-13 magnetic resonance spectrum as shown in FIG. XVIII of the drawings with significant peaks at
   16.5; 16.9; 17.6; 20.2; 20.9; 25.7; 25.9; 26.8; 35.7; 36.4; 36.6; 36.7; 53.0; 59.0; 62.3; 62.8; 62.9; 63.2; 63.8; 66.8; 67.9; 68.8; 69.2; 69.4; 70.5; 74.4; 84.0; 85.0; 94.7; 95.2; 97.6; 101.0; 105.9; 107.8; 108.2; 113.5; 114.1; 16.9; 126.7; 135.5; 142.5; 145.2; 152.3; 162.4; 170.3; 203.4.

8. Antitumor agent LL-D49194ζ, a composition which:
(a) is effective as an antitumor agent;
(b) is effective as an antibacterial agent; and
(c) has ultraviolet absorption spectra as shown in FIG. XIX of the drawings.

9. Antitumor agent LL-D49194η, a composition which:
(a) is effective as an antitumor agent;
(b) is effective as an antibacterial agent;
(c) has a specific rotation;
   $[\alpha]_D^{26} = +65 \pm 3°$ (0.4%, ethanol);
(d) has ultraviolet absorption spectra as shown in FIG. XX of the drawings;
(e) has an infrared absorption spectrum as shown in FIG. XXI of the drawings;
(f) has a proton magnetic resonance spectrum as shown in FIG. XXII of the drawings; and
(g) has a carbon-13 magnetic resonance spectrum as shown in FIG. XXIII of the drawings with significant peaks at
   16.7; 16.9; 20.3; 20.9; 25.7; 26.0; 34.6; 36.7; 47.8; 52.8; 52.8; 58.6; 62.7; 62.9; 63.6; 67.5; 67.9; 68.8; 69.0; 69.1; 69.9; 71.3; 74.4; 94.3; 94.9; 98.0; 102.3; 104.3; 107.3; 114.8; 115.0; 116.7; 126.5; 135.5; 142.9; 144.8; 151.6; 163.2; 170.3; 202.8.

10. Antitumor agent LL-D49194ω₁, a composition which:
(a) is effective as an antitumor agent;
(b) is effective as an antibacterial agent;
(c) has ultraviolet absorption spectra as shown in FIG. XXVII of the drawings;
(d) has a proton magnetic resonance spectrum as shown in FIG. XXVIII of the drawings; and
(e) has a carbon-13 magnetic resonance spectrum as shown in FIG. XXIX of the drawings with significant peaks at
   16.5; 16.9; 17.6; 20.1; 26.2; 26.8; 35.7; 35.8; 36.0; 36.7; 53.0; 58.8; 62.2; 62.7; 63.6; 63.9; 67.2; 68.0;

69.3; 69.4; 70.0; 70.1; 70.6; 74.4; 84.0; 85.1; 94.8; 95.2; 98.0; 101.0; 106.0; 107.9; 108.3; 113.5; 114.1; 116.9; 127.1; 135.6; 142.4; 145.2; 152.4; 162.3; 203.5.

11. Antitumor agent LL-D49194$\omega_2$, a composition which:
   (a) is effective as an antitumor agent;
   (b) is effective as an antibacterial agent; and
   (c) has ultraviolet absorption spectra as shown in FIG. XXX of the drawings.

12. Antitumor agent LL-D49194$\omega_3$, a composition which:
   (a) is effective as an antitumor agent;
   (b) is effective as an antibacterial agent;
   (c) has a specific rotation;
      $[\alpha]_D^{26} = 0°$ (0.6%, ethanol):
   (d) has ultraviolet absorption spectra as shown in FIG. XXXI of the drawings;
   (e) has an infrared absorption spectrum as shown in FIG. XXXII of the drawings;
   (f) has a proton magnetic resonance spectrum as shown in FIG. XXXIII of the drawings; and
   (g) has a carbon-13 magnetic resonance spectrum as shown in FIG. XXXIV of the drawings with significant peaks at
   16.7; 16.9; 20.2; 20.9; 25.7; 26.1; 34.7; 36.5; 36.7; 53.0; 58.8; 62.3; 62.8; 62.9; 63.6; 66.8; 67.9; 68.8; 69.4; 69.9; 70.5; 74.4; 85.1; 94.8; 95.3; 97.5; 106.0; 107.9; 108.3; 113.6; 114.0; 116.9; 126.7; 135.5; 142.5; 145.1; 152.3; 162.4; 170.3; 203.5.

13. A method of treating bacterial infections in warm-blooded animals which comprises administering to said animals an antibacterially effective amount of a compound selected from the group consisting of LL-D49194$\alpha_1$, LL-D49194$\beta_1$, LL-D49194$\beta_2$, LL-D49194$\beta_3$; LL-D49194$\epsilon$; LL-D49194$\delta$; LL-D49194$\epsilon$; LL-D49194$\zeta$; LL-D49194$\eta$; LL-D49194$\omega_1$; LL-D49194$\omega_3$.

14. A method of inducing regression of leukemia and/or inhibiting the growh of tumors in a mammal comprising administering to said mammal an effective amount of a compound selected from the group consisting of LL-D49194$\alpha_1$; LL-D49194$\beta_1$; LL-D49194$\beta_2$; LL-D49194$\beta_3$; LL-D49194$\epsilon$; LL-D49194$\delta$; LL-D49194$\epsilon$; LL-D49194$\zeta$; LL-D49194$\eta$; LL-D49194$\omega_1$; LL-D49194$\omega_2$ and LL-D49194$\omega_3$.

15. A process for producing antibiotics LL-D49194$\alpha_1$; LL-D49194$\beta_1$; LL-D49194$\beta_2$; LL-D49194$\beta_3$; LL-D49194$\gamma$; LL-D49194$\delta$; LL-D49194$\epsilon$; LL-D49194$\zeta$; LL-D49194$\eta$; LL-D49194$\omega_1$; LL-D49194$\omega_2$ and LL-D49194$\omega_3$ which comprises aerobically fermenting the organism *Streptomyces vinaceus-drappus* NRRL 15735 or mutants thereof in a liquid medium containing assimilable sources of carbon, nitrogen and inorganic salts, until substantial antibiotic activity is imparted to said medium and then recovering the antibiotics therefrom.

16. A process for producing antibiotics LL-D49194$\alpha_1$; LL-D49194$\beta_1$; LL-D49194$\beta_2$; LL-D49194$\beta_3$; LL-D49194$\gamma$; LL-D49194$\delta$; LL-D49194$\epsilon$; LL-D4194$\zeta$; LL-D49194$\eta$; LL-D49194$\omega_1$; LL-D49194$\omega_2$ and LL-D49194$\omega_3$ which comprises aerobically fermenting a liquid medium containing assimilable sources of carbon, nitrogen and inorganic salts; which medium has been inoculated with a viable culture of the organism *Streptomyces vinaceus-drappus* NRRL 15735 or mutants thereof, maintaining said fermentation culture at a temperature of 24°–32° C. for a period of 90–200 hours, harvesting the mesh and extracting the antibiotics.

17. A biologically pure culture of the microorganism *Streptomyces vinaceus-drappus* having the identifying characteristics of NRRL 15735, said culture being capable of producing antibiotics LL-D49194$\alpha_1$; LL-D49194$\beta_1$; LL-D49194$\beta_2$; LL-D49194$\beta_3$; LL-D49194$\gamma$; LL-D49194$\delta$; LL-D49194$\epsilon$; LL-D49194$\zeta$; LL-D49194$\eta$; LL-D49194$\omega_1$; LL-D49194$\omega_2$ and LL-D49194$\omega_3$ in recoverable quantities upon fermentation in an aqueous nutrient medium containing assimilable sources of carbon, nitrogen and inorganic substances.

18. A biologically pure culture of the microorganism *Streptomyces vinaceus-drappus* according to claim 17, wherein said microorganism has spontaneously mutated such that the microorganism is genetically altered but still retains the ability to synthesize antibiotics LL-D49194$\alpha_1$; LL-D49194$\beta_1$; LL-D49194$\beta_2$; LL-D49194$\beta_3$; LL-D49194$\gamma$; LL-D49194$\delta$; LL-D49194$\epsilon$; LL-DL49194$\zeta$; LLl-D49194$\eta$; LL-D49194$\omega_1$; LL-D49194$\omega_2$ and LL-D49194$\omega_3$.

19. A biologically pure culture of the microorganism *Streptomyces vinaceus-drappus* according to claim 17, wherein said microorganism has been subjected to mutagenic means such that the microorganism is genetically altered but still retains the ability to synthesize antibiotics LL-D49194$\alpha_1$; LL-D49194$\beta_1$; LL-D49194$\beta_2$; LL-D49194$\beta_3$; LL-D49194$\gamma$; LL-D49194$\delta$; LL-D49194$\epsilon$; LL-D49194$\zeta$; LL-D49194$\eta$; LL-D49194$\omega_1$; LL-D49194$\omega_2$ and LLl-D49194$\omega_3$.

* * * * *